(12) United States Patent
Scheinberg et al.

(10) Patent No.: US 7,488,718 B2
(45) Date of Patent: Feb. 10, 2009

(54) SYNTHETIC HLA BINDING PEPTIDE ANALOGUES AND USES THEREOF

(75) Inventors: David Scheinberg, New York, NY (US); Javier Pinilla-Ibarz, New York, NY (US)

(73) Assignee: Sloan Kettering Institue for Cancer Research, New York, NY (US)

( * ) Notice: Subject to any disclaimer, the term of this patent is extended or adjusted under 35 U.S.C. 154(b) by 477 days.

(21) Appl. No.: 10/999,425

(22) Filed: Nov. 30, 2004

(65) Prior Publication Data

US 2005/0119185 A1 Jun. 2, 2005

Related U.S. Application Data

(60) Provisional application No. 60/525,955, filed on Dec. 1, 2003.

(51) Int. Cl.
*A61K 38/08* (2006.01)
*C07K 7/06* (2006.01)
(52) U.S. Cl. .......................................... 514/15; 530/328
(58) Field of Classification Search ........................ None
See application file for complete search history.

(56) References Cited

U.S. PATENT DOCUMENTS 6,156,316 A 12/2000 Scheinberg et al.

FOREIGN PATENT DOCUMENTS

WO WO 01/62920 8/2001

OTHER PUBLICATIONS

Nieda, M , et al., Dendritic cells stimulate the expansion of bcr-abl specific CD8+ T cells with cytotoxic activity against leukemic cells from patients with chronic myeloid leukemia Blood. 1998 91(3): p. 977-83.
ten Bosch, G J., et al , A BCR-ABL oncoprotein p210b2a2 fusion region sequence is recognized by HLA-DR2a restricted cytotoxic T lymphocytes and presented by HLA-DR matched cells transfected with an li(b2a2) construct Blood. 1999 94(3): p. 1038-45.
Yotnda, P , et al , Cytotoxic T cell response against the chimeric p210 BCR-ABL protein in patients with chronic myelogenous leukemia J Clin Invest, 1998 101(10): p. 2290-6.
Pinilla-Ibarz. J., et al, Vaccination of patients with chronic myelogenous leukemia with bcr-abl oncogene breakpoint fusion peptides generates specific immune responses. Blood. 2000 95(5): p. 1781-7.
Cathcart. K . et al . All CML patients vaccinated with a multivalent bcr-abl peptide vaccine show specific immune responses in a phase II trial Blood. 2001 98(11): p. 728a-728a.
Cathcart. K , et al., A multivalent bcr-abl fusion peptide vaccination trial in patients with chronic myeloid leukemia Blood. 2003.
Dyall R, Bowne WB, Weber LW, LeMaoult J, Szabo P, Moroi Y, et al Heteroclitic immunization induces tumor immunity J Exp Med 1998; 188:1553-61.
Zugel. U . et al , Termination of peripheral tolerance to a T cell epitope by heteroclitic antigen analogues. J Immunol. 1998 161(4): p. 1705-9.
Pinilla-Ibarz, J , et al . Synthetic analogue bcr/abl fusion peptides improve class I Immunogenicity to the native protein Blood. 2000 96(11): p. 510a-510a.
Clay TM. Custer MC, McKee MD. Parkhurst M, Robbins PF. Kerstann K. et al Changes in the fine specificity of gp100(209-217)-reactive T cells in patients following vaccination with a peptide modified at an HLA-A2.1 anchor residue. J Immunol 1999:162: 1749-55.
Parkhurst MR, Saigalier ML. Southwood S. Robbins PF, Setle A, Rosenberg SA. et al Improved induction of melanoma-reactive CTL with peptides from the melanoma antigen gp100 modified at HLA-A 0201-binding residues. J Immunol 1996; 157:2539-48.
Rosenberg SA. Yang JC. Schwartzentruber DJ, Hwu P. Marincola FM, Topalian SL, et al Immunologic and therapeutic evaluation of a synthetic peptide vaccine for the treatment of patients with metastatic melanoma Nat Med 1998; 4:321-7.
Slansky JE, Rattis FM, Boyd LF. Fahmy T. Jaffee EM, Schneck JP, et al. Enhanced antigen-specific antitumor immunity with altered peptide ligands that stabilize the MHC-peptide-TCR complex immunity 2000; 13:529-38.
Nicholson LB, Waldner H. Carrizosa AM, Sette A, Collins M. Kuchroo VK Heteroclitic proliferative responses and changes in cytokine profile induced by altered peptides: implications for autoimmunity Proc Natl Acad Sci USA 1998:95:264-9.
Valmori D, Fonteneau JF, Valitutti S. Gervois N. Dunbar R. Lienard D, et al. Optimal activation of tumor-reactive T cells by selected antigenic peptide analogues Int Immunol 1999;1971-80.
Kessler et al, Effects of epitope modification on T cell receptor-ligand binding and antigen recognition by seven H-2Kd-restricted cytotoxic T lymphocyte clones specific for a photoreactive peptide derivative. J Exp Med. Feb. 17, 1997;185(4):629-40.

*Primary Examiner*—Anish Gupta
(74) *Attorney, Agent, or Firm*—Pearl Cohen Zedek Latzer, LLP; Mark S. Cohen

(57) ABSTRACT

The present invention provides synthetic peptides comprising at least analogues of a native peptide that specifically bind to HLA A0201 or HLA A0301 molecules on a cell characteristic of a pathophysiologic state, such as a cancer cell, in a mammal. Also provided are pharmaceutical compositions and immunogenic compositions comprising at least the peptide analogue segments or a DNA encoding the same. Also provided are methods of using the synthetic peptides and immunogenic compositions to induce a heteroclitic immune response or to treat a cancer.

10 Claims, 13 Drawing Sheets

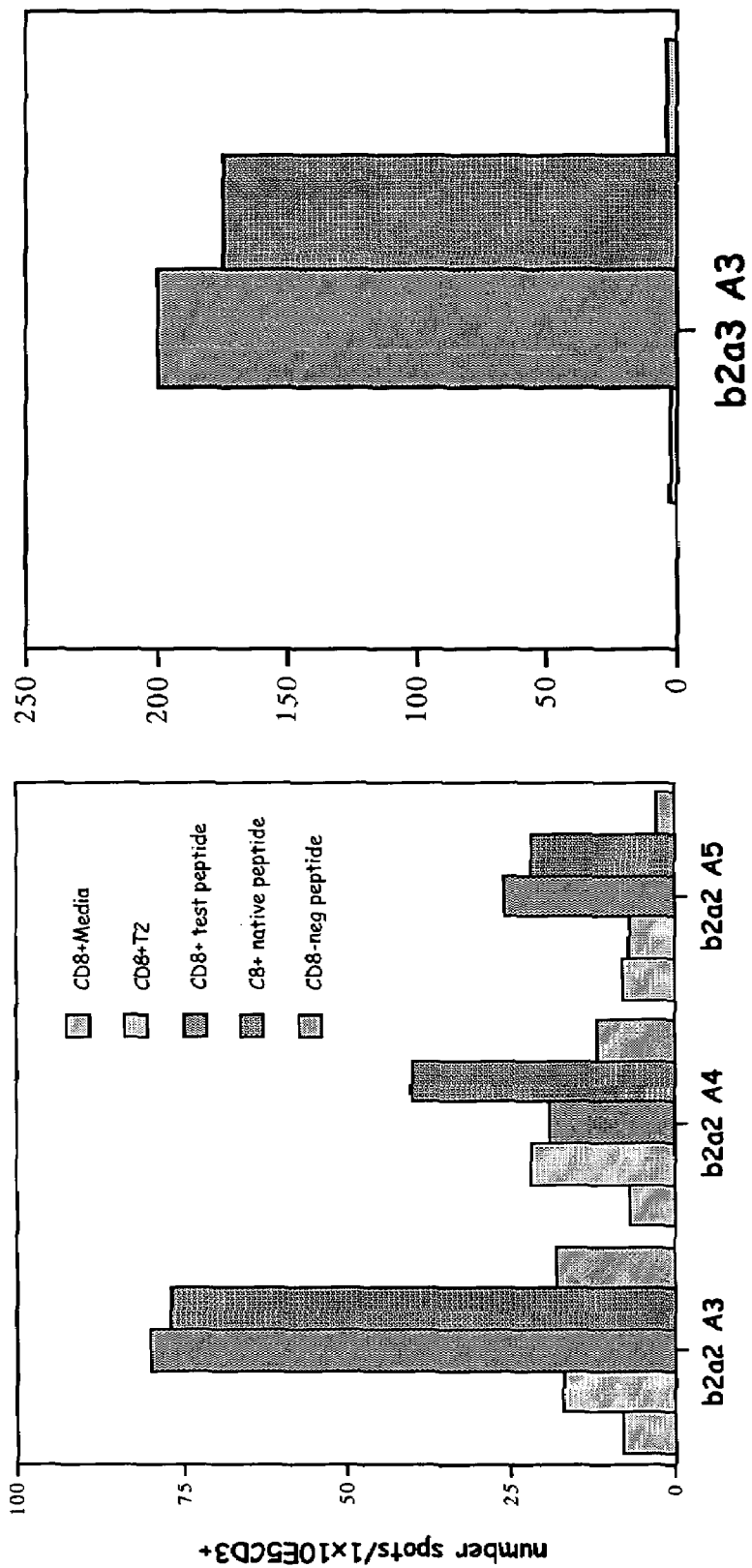

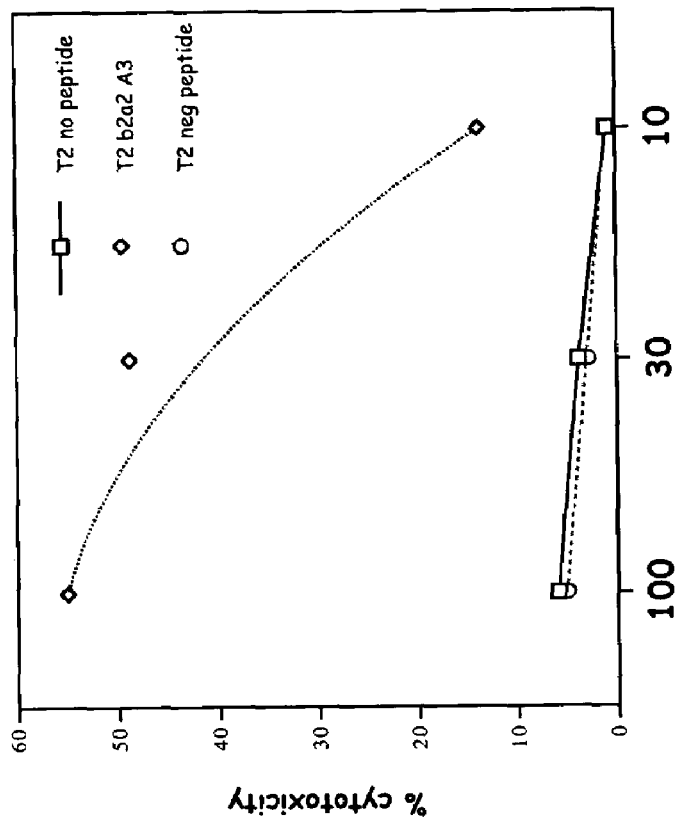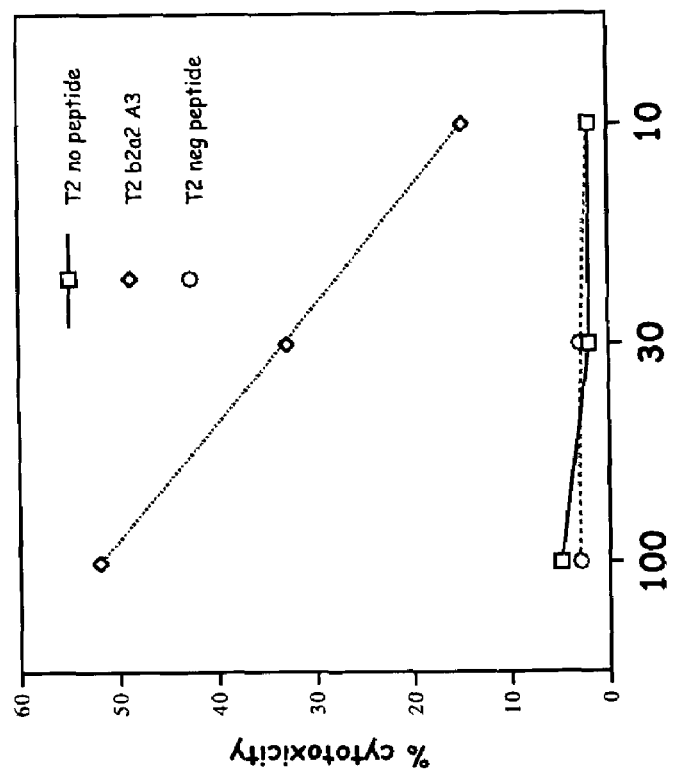
Fig. 4B

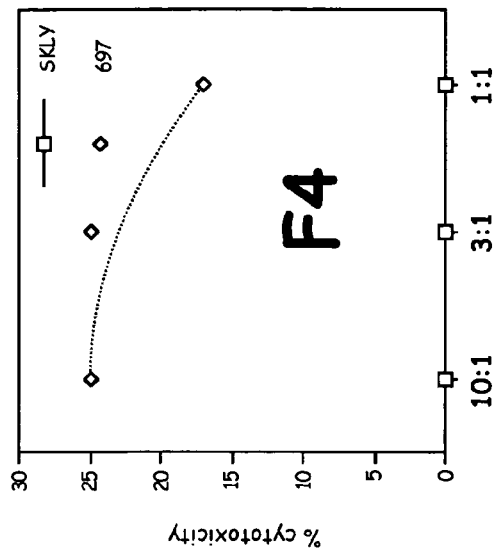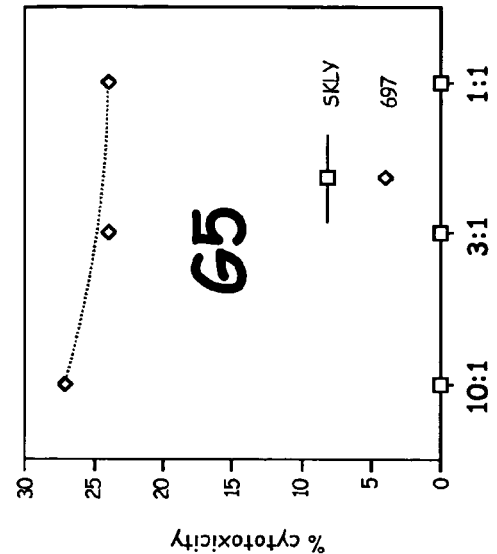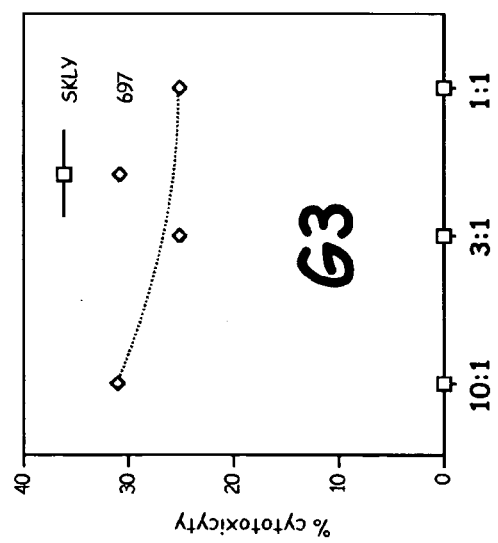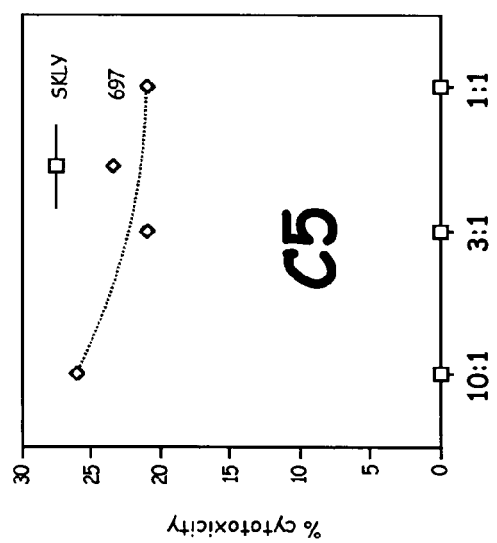
Fig. 8B

SYNTHETIC HLA BINDING PEPTIDE ANALOGUES AND USES THEREOF

CROSS-REFERENCE TO RELATED APPLICATIONS

This non-provisional application claims benefit of priority of provisional U.S. Ser. No. 60/525,955, filed Dec. 1, 2003, now abandoned.

FEDERAL FUNDING LEGEND

This invention was produced in part using funds obtained through National Cancer Institute Core Grant No. 08748 and National Institutes of Health Grant Nos. PO1 33049 and PO1 2376. Consequently, the federal government has certain rights in this invention.

BACKGROUND OF THE INVENTION

1. Field of the Invention

This invention relates to the fields of immunology and leukemia therapy. More specifically, this invention relates to the use of synthetic analogue peptides to induce heteroclitic human T cell responses against native peptides of the synthetic analogues.

2. Description of the Related Art

Chronic myelogenous leukemia (CML) is a pluripotent stem cell disorder characterized by the presence of the Philadelphia chromosome (Ph). The Philadelphia chromosome represents a translocation in which the c-abl oncogene has moved from chromosome 9 into the breakpoint cluster region (bcr) within the bcr gene on chromosome 22, resulting in a chimeric bcr-abl gene. The fused genes encode an 8.5 kb chimeric mRNA which is usually translated into a 210-kDa or 190-kDa protein. This bcr-abl protein is a tyrosine-kinase which is uniquely present in the leukemia cells of chronic myelogenous leukemia patients and is necessary and sufficient for transformation.

In chronic myelogenous leukemia, the breakpoint in the bcr gene occurs either between bcr exon 2 (b2) and 3 (b3) or between bcr exon 3(b3) and 4(b4). Although aberrant bcr-abl fusion genes and bcr-abl mRNA splicing can occur, the majority of patients with chronic myelogenous leukemia therefore express p210-b3a2 or p210-b2a2; often both p210 and p 190 proteins are expressed together with low levels of p 190-e 1 a2 bcr-abl proteins. In Ph1 positive acute lymphocytic leukemia (ALL), the predominant breakpoint is at the e1a2 site.

The chimeric fusion proteins are potential antigens. First, the proteins are uniquely expressed in chronic myelogenous leukemia cells in which the junctional regions contain a sequence of amino acids that is not expressed on any normal protein. Secondly, as a result of the codon split on the fused message, a new amino acid, lysine in b3a2, and a conserved amino acid, glutamic acid in b2a2, is present at the exact fusion point in each of the proteins. Therefore, the unique amino acid sequences encompassing the b3a2 and b2a2 breakpoint region can be considered truly tumor specific antigens. Despite the intracellular location of these proteins, short peptides produced by cellular processing of the products of the fusion proteins can be presented on the cell surface within the cleft of HLA molecules and in this form they can be recognized by T cells.

Recent clinical trials demonstrated that a tumor specific, bcr-abl derived multivalent vaccine may be safely administered to patients with chronic phase chronic myelogenous leukemia. The vaccine reliably elicits a bcr-abl peptide-specific CD4 immune response as measured by DTH in vivo, by CD4+ T cell proliferation ex vivo and by gamma interferon secretion in an ELISPOT assay. However, no CD8 responses in HLA A0201 patients and only weak responses in HLA A0301 patients were detected using a sensitive gamma interferon ELISPOT assay.

Wilms tumor protein 1 (WT1) is a zinc finger transcription factor expressed during normal ontogenesis such as in fetal kidney, testis and ovary. In adults, WT1 expression is limited to low levels on hematopoietic stem cells, myoepithelial progenitor cells, renal podocytes and some cells in testis and ovary. Recent demonstration that WT1 is overexpressed in several types of leukemia suggested that WT1 would be an attractive target for immunotherapy. Three peptide nonamers from WT1 have been identified to generate a WT1 specific cytotoxic response in the context of HLA 0201 and HLA 2402. However, as WT1 protein is a self-antigen, breaking tolerance is a potential concern.

For stimulation of responses the strength of CD8 responses depends upon the binding affinity of the target peptide to class I MHC molecules, the peptide-HLA complex stability, and the avidity of the T cell receptor binding for the peptide complex. Killing of native CML cells also requires adequate processing and presentation of the natural antigen. Therefore the lack of reproducible CD8 responses in these clinical trials could be the result of the biochemistry of these class I peptide-HLA interactions, which results in their weak immunogenicity to cytotoxic CD8 cells. None of the native CML peptides reported to bind to human MHC bound the HLA pocket with high affinity. This may explain, in part, the lack of a detectable immune response to bcr-abl peptides as proteins seen in patients with chronic myelogenous leukemia despite the appearance of this antigen in the CML cells.

In some antigenic systems peptide analogues are used to circumvent a poor immunogenic response. A high correlation has been found between overall analogue peptide affinities for MHC class I molecules and in vivo peptide immunogenicity in HLA-A2Kb transgenic mice. A better correlation with a peptide's ability to form stable HLA-A0201 complexes and immunogenicity has been reported. Improved immunogenicity in HLA-A0201/Kb transgenic mice also has been reported for analogues of a self-peptide, gp100154-162, displaying both higher affinity and more prolonged complex stability than the natural peptide.

To design peptide analogues several successful algorithms have been utilized in which large protein sequences are scanned for the presence of suitable binding motifs, leading to the identification of predicted antigens that have subsequently been experimentally validated. Analogs of antigenic peptides have been formulated by direct modifications of MHC anchor positions, which are referred to as "MHC anchor-modified ligands", or modifications of TCR contact sites, which generally are termed "altered peptide ligands". The identification of peptide epitope analogues that strengthen the stability of the MHC-peptide complex in vivo and in vitro is thought to enhance the potency of intrinsically weak immunogenic peptides for the activation and amplification of relevant T-cell subsets. This concept was originally described in a murine CD4+ T cell model using HIV peptides (1), and now has been extended to a variety of viral and tumor immunological systems.

Artificial variants of MHC class I-binding self-peptides have been designed (2). Since these variant peptides were foreign to the host immune system, a strong CTL response was induced. Unlike weak T cell responses to self-peptide-MHC complexes, CTL responses to variant peptides can be sustained for a longer period without causing annihilation of the clones due to insufficient signals for cell division or survival. Since a substantial fraction of such CTLs cross-react with non-mutated self-peptides expressed in tumor cells in much smaller amounts, immunization with variant peptides may be a more efficient method to induce CTLs against tumors. The scoring system for MHC class I-binding peptides should provide a convenient method for design of cross-reactive self-mimicking peptides for immunization.

The improved immunogenicity in vivo and relevance of MHC anchor-modified ligands was first shown formally in human neoplastic disease in a controlled study of patients with malignant melanoma using a melanoma-associated A0201 restricted peptide derived from gp100. It has been shown recently with HLA-tetramer based detection methods that the parental Melan-A antigenic peptides are weak agonists which activate antigen-specific T cells suboptimally (3). In contrast, melan A peptide analogues were identified that behaved as full agonists and induced full T cell activation leading to strong tumor antigen-specific CTL responses (4).

Simple motifs and the statistical binding matrices can be used to perform a crude search for MHC-binding peptides. Unfortunately, the presence of a simple sequence motif does not correlate well with binding. Therefore these simple motifs are not always necessary or sufficient for binding. Only 30% of the peptides that carry such simple motifs bind well when examined in a biochemical binding assay. Predictions of binding can be improved considerably when extended motifs are used, rather than the simple motifs. About 70% of the peptides carrying an extended motif bind well.

Assuming that each amino acid in each position contributes a certain binding energy independent of the neighboring residues and that the binding of a given peptide is the result of combining the contributions from the different residues, multiplying the relevant matrix values should give an indication of the binding of the corresponding peptide. Such statistical matrix-driven predictions have been somewhat more successful, thereby suggesting that MHC binding is to some extent the result of a combinatorial specificity. The identification of analogues peptides based on these methods has been applied recently to the identification of CTL epitopes deduced from proteinase 3, melanoma antigen 3, mucin 1 and telomerase.

The weak immunogenicity of native bcr-abl fusion peptides, as demonstrated by poor lysis of the cells, or the problem of tolerance using native peptides from a self-antigen, such as WT1, has prevented use of these native peptides as an effective vaccine against CML. A need exists in the art to develop therapeutic strategies using vaccination against a truly tumor specific antigen that is also the oncogenic protein required for neoplasia. There is a need for improved synthetic peptide analogues designed to elicit a greater immunogenic response.

The prior art is deficient in the lack of synthetic analogue peptides that could generate an immune response that not only recognizes the immunizing epitopes, but that also cross reacts with the original native peptides. Specifically, the prior art is deficient in synthetic peptide analogs with both improved HLA binding and improved ability to elicit a greater immunogenic response against cancer cells. The present invention fulfills this longstanding need and desire in the art.

SUMMARY OF THE INVENTION

The present invention is directed to a synthetic peptide comprising a sequence of amino acids containing at least a segment that is an analogue of a native peptide that specifically binds to HLA A0201 or HLA A0301 molecules on a cell characteristic of a pathophysiologic state in a mammal. The synthetic peptide may be derived from native peptides comprising a breakpoint region of the bcr-abl fusion protein or of the WT1 protein.

The present invention also is directed to a related synthetic peptide with an amino acid sequence selected from YLKALQRPV (SEQ ID NO: 2), KQSSKALQV (SEQ ID NO: 4), KLSSKALQV (SEQ ID NO: 5), KLLQRPVAV (SEQ ID NO: 7), TLFKQSSKV (SEQ ID NO: 9), YLFKQSSKV (SEQ ID NO: 10), LLINKEEAL (SEQ ID NO: 12), LTINKVEAL (SEQ ID NO: 13), YLINKEEAL (SEQ ID NO: 14), YLINKEEAV (SEQ ID NO: 15), or YLINKVEAL (SEQ ID NO: 16), NMYQRNMTK (SEQ ID NO: 36), NMHQRVMTK (SEQ ID NO: 37), NMYQRVMTK (SEQ ID NO: 38), QMYLGATLK (SEQ ID NO: 40), QMNLGVTLK (SEQ ID NO: 41), QMYLGVTLK (SEQ ID NO: 42), FMYAYPGCNK (SEQ ID NO: 44), FMCAYPFCNK (SEQ ID NO: 45), FMYAYPFCNK (SEQ ID NO: 46), KLYHLQMHSR (SEQ ID NO: 48), KLSHLQMHSK (SEQ ID NO: 49), or KLYHLQMHSK (SEQ ID NO: 50).

The present invention also is directed to pharmaceutical composition comprising a therapeutically effective amount of the synthetic peptides described herein or a DNA encoding the synthetic peptide and a suitable carrier.

The present invention is directed further to an immunogenic composition comprising an immunogenically effective amount of the synthetic peptide described herein and a pharmaceutically acceptable carrier, adjuvant or diluent or a combination thereof.

The present invention is directed further still to a method of treating a cancer in a human. The pharmaceutical compositions described herein are administered to the human. A heteroclitic response is induced by cytotoxic T-cells that recognize at least the analogue segment of the synthetic peptides described herein against cancer cells presenting a native peptide from which the analogue segment is derived. Thus, the cytotoxic T-cells recognize or kill the cancer cells thereby treating the cancer. In a related method the present invention is directed to a method of treating leukemia in a human using the pharmaceutical compositions comprising the synthetic peptide containing at least the analogue segment derived from a native peptide of a WT1 protein or a DNA encoding the synthetic peptide.

The present invention is directed further still to a method of inducing formation and proliferation of human cytotoxic T cells that produce a heteroclitic immune response against cancer cells. Human immune cells are contacted with a synthetic peptide containing at least the analogue segment described herein. Thereby the formation and proliferation of human cytotoxic T cells reactive against the activated cells presenting the analogue segment of the synthetic peptide is induced. The proliferating T cells will cross react with the cancer cells presenting a native peptide from which the analogue segment is derived such that the human cytotoxic T cells are thereby produce a heteroclitic immune response against the cancer cells. The present invention also is directed further to a related method of inducing formation and proliferation of human cytotoxic T cells that produce a heteroclitic immune response against leukemic cells in a human as described in the method for inducing formation and proliferation of cytotoxic T cells against a cancer cell.

The present invention is directed to a related method of inducing a heteroclitic response in a human. The immunogenic compositions described herein are administered to a human to activate human immune cells. The formation and proliferation of cytotoxic T cells against the activated cells presenting the analogue segment of the synthetic peptide described herein that comprises the immunogenic composition is induced thereby. The cytotoxic T cells will cross-react with a cancer cell presenting a native peptide from which the analogue segment is derived to induce the heteroclitic response. The present invention is directed further to a related method of inducing a heteroclitic response in a human against leukemic cells as described in the method for inducing such heteroclitic response against a cancer cell.

Other and further aspects, features, benefits, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention are briefly summarized. Details of the above may be had by reference to certain embodiments thereof which are illustrated in the appended drawings. These drawings form a part of the specification. It is to be noted; however, that the appended drawings illustrate preferred embodiments of the invention and therefore are not to be considered limiting in their scope.

FIGS. 3A-3B show the results of a CD3+ gamma interferon ELISPOT from a healthy HLA A0201 donor using the b2a2 A3-A5 peptides (FIG. 3A) and from a chronic myelogenous leukemia patient in chronic phase HLA A0201 (FIG. 3B) using the b2a2 A3 peptide.

FIGS. 4A-4B show the results of cytotoxicity assays with T cells from a healthy HLA A0201 donor using p210C, p210F and p190B peptides (FIG. 4A) and the b2a2 A3 peptide (FIGS. 4B).

FIGS. 8A-8B show the results of cytotoxicity assays using CD8+ T cells stimulated with synthetic WT-1 A1 peptides from a HLA A0201 donor against HLA matched CML blasts presenting native peptide sequences.

DETAILED DESCRIPTION OF THE INVENTION

Figure 1A:
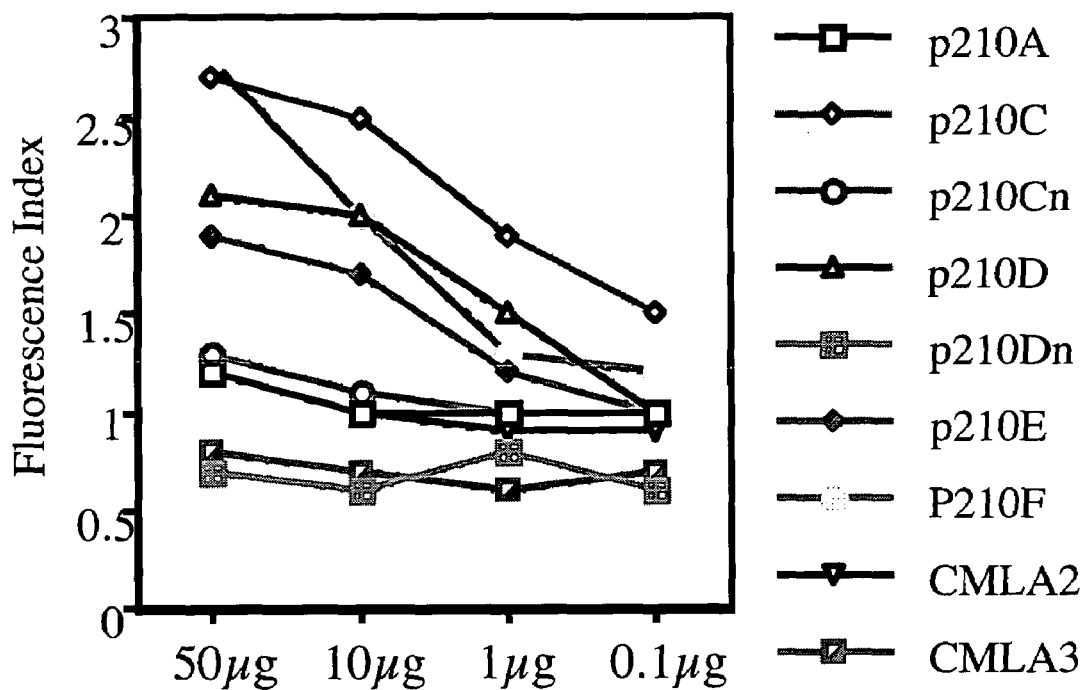
FIGS. 1A-1B show T2 stabilization assays using peptides derived from b3a2 translocation (FIG. 1A) and b2a2 translocation (FIG. 1B).

In one embodiment of the present invention, there is provided a synthetic peptide comprising a sequence of amino acids containing at least a segment that is analogue of a native peptide that specifically binds HLA A0201 or HLA A0301 molecules on a cell characteristic of a pathophysiologic state in a mammal. In this embodiment the analogue segment may have a number of amino acids that is about 70% to about 130% of the number of amino acids in the native peptide. The number of amino acids may be about 8 to about 12.

In all aspects of this invention the pathophysiologic state may be a cancer. The cancer may be a leukemia such as a chronic myelogenous leukemic. Alternatively, the cancer may breast cancer, lymphoma, mesothelioma, lung cancer, testicular cancer, or ovarian cancer. Additionally, in all aspects the mammal may be a human.

Furthermore, in all aspects of this embodiment the synthetic peptide may comprise an immunogenic carrier linked thereto. Examples of carriers are a protein, a peptide or an antigen-presenting cell. Representative examples of a protein or peptide are keyhole limpet hemocyanin, an albumin or a polyamino acid. A representative example of an antigen-presenting cell is a dendritic cell.

In one aspect of this embodiment the amino acids comprise a precursor to the analogue segment which is a degradation product thereof. In this aspect the presursor may be a bcr-abl fusion protein where the analogue segment spans the breakpoint region of the fusion protein. Alternatively, the precursor may be WT1 where the analogue segment replaces a native peptide of WT1.

In a related aspect, the analogue segment is derived from a native peptide comprising a breakpoint region of a bcr-abl fusion protein. The native peptide may be a native p190-31a2 peptide. The native peptide may be a native p210-b3a2 peptide and the amino acid sequence of the analogue segment may be YLKALQRPV (SEQ ID NO: 2), KQSSKALQV (SEQ ID NO: 4), KLSSKALQV (SEQ ID NO: 5), KLLQRPVAV (SEQ ID NO: 7), TLFKQSSKV (SEQ ID NO: 9), or YLFKQSSKV (SEQ ID NO: 10). Preferably, the amino acid sequence is YLKALQRPV (SEQ ID NO: 2), KLLQRPVAV (SEQ ID NO: 7) or YLFKQSSKV (SEQ ID NO: 10)

Alternatively, the native peptide may be a native p210-b2a2 peptide and the amino acid sequence of the analogue segment may be LLINKEEAL (SEQ ID NO: 12), LTINKVEAL (SEQ ID NO: 13), YLINKEEAL (SEQ ID NO: 14), YLINKEEAV (SEQ ID NO: 15), and YLINKVEAL (SEQ ID NO: 16). Preferably the amino acid sequence is YLINKEEAL (SEQ ID NO: 14).

In another aspect of this embodiment, the analogue segment is derived from a native peptide comprising a WT1 protein. The amino acid sequence of the WT1 derived analogue segment may be YMFPNAPYL (SEQ ID NO: 18), YLGEQQYSV (SEQ ID NO: 20), YLLPAVPSL (SEQ ID NO: 22), YLGATLKGV (SEQ ID NO: 24), YLNALLPAV (SEQ ID NO: 26), GLRRGIQDV (SEQ ID NO: 28), KLYFKLSHL (SEQ ID NO: 30), ALLLRTPYV (SEQ ID NO: 32), YMTWNQMNL (SEQ ID NO: 34), NMYQRNMTK (SEQ ID NO: 36), NMHQRVMTK (SEQ ID NO: 37), NMYQRVMTK (SEQ ID NO: 38), QMYLGATLK (SEQ ID NO: 40), QMNLGVTLK (SEQ ID NO: 41), QMYLGVTLK (SEQ ID NO: 42), FMYAYPGCNK (SEQ ID NO: 44), FMCAYPFCNK (SEQ ID NO: 45), FMYAYPFCNK (SEQ ID NO: 46), KLYHLQMHSR (SEQ ID NO: 48), KLSHLQMHSK (SEQ ID NO: 49), and KLYHLQMHSK (SEQ ID NO: 50).

In a related embodiment of this invention there is provided a synthetic peptide with an amino acid sequence that may be one or more of YLKALQRPV (SEQ ID NO: 2), KQSSKALQV (SEQ ID NO: 4), KLSSKALQV (SEQ ID NO: 5), KLLQRPVAV (SEQ ID NO: 7), TLFKQSSKV (SEQ ID NO: 9), YLFKQSSKV (SEQ ID NO: 10), LLINKEEAL (SEQ ID NO: 12), LTINKVEAL (SEQ ID NO: 13), YLINKEEAL (SEQ ID NO: 14), YLINKEEAV (SEQ ID NO: 15), or YLINKVEAL (SEQ ID NO: 16). Alternatively, a synthetic peptide is provided with an amino acid sequence that may be one or more of NMYQRNMTK (SEQ ID NO: 36), NMHQRVMTK (SEQ ID NO: 37), NMYQRVMTK (SEQ ID NO: 38), QMYLGATLK (SEQ ID NO: 40), QMNLGVTLK (SEQ ID NO: 41), QMYLGVTLK (SEQ ID NO: 42), FMYAYPGCNK (SEQ ID NO: 44), FMCAYPFCNK (SEQ ID NO: 45), FMYAYPFCNK (SEQ ID NO: 46), KLYHLQMHSR (SEQ ID NO: 48), KLSHLQMHSK (SEQ ID NO: 49), or KLYHLQMHSK (SEQ ID NO: 50).

In another related embodiment there is provided a pharmaceutical composition comprising a therapeutically effective amount of the synthetic peptide of claim 1 or a DNA encoding the synthetic peptide; and a pharmaceutically acceptable carrier. In aspects of this embodiment where the pharmaceutical composition comprises a DNA encoding the synthetic peptide, the DNA may be inserted into a vector or into an antigen-presenting cell. An example of an antigen presenting cell is a dendritic cell.

In one aspect of this embodiment an analogue segment comprising the synthetic peptide is derived from a native p210-b3a2 peptide, a native p210-b2a2 peptide or a native p190-e1a2 peptide. The amino acid sequences for these analogue segments are as identified supra for p210-b3a2 and p210-b2a2 derived analogues. In a related aspect of this embodiment an analogue segment comprising the synthetic peptide is derived from a native peptide comprising the WT-1 protein. These amino acid sequences for these WT1-derived analogue segments are as identified supra for WT-1 derived analogues.

In still another related embodiment of the present invention, there is provided an immunogenic composition comprising an immunogenically effective amount of the synthetic peptides described supra and a pharmaceutically acceptable carrier, adjuvant or diluent or a combination thereof. The carrier may be a protein, a peptide or an antigen-presenting cell linked to the synthetic peptide. Examples of a protein or peptide carrier are keyhole limpet hemocyanin, an albumin or a polyamino acid. An example of an antigen-presenting cell is a dendritic cell. The synthetic peptides and analogue segments comprising the synthetic peptides are as described supra. In aspects of this embodiment, the analogue segments may be derived from those native peptides and the amino acid sequences may be those sequences described supra for a pharmaceutical composition.

In another embodiment of the present invention, there is provided a method of inducing formation and proliferation of human cytotoxic T cells that produce a heteroclitic immune response against cancer cells, comprising contacting human immune cells with the synthetic peptides described supra to activate the immune cells; and inducing formation and proliferation of human cytotoxic T cells reactive against the activated cells presenting at least the analogue segment of the synthetic peptide, where the proliferating T cells will cross react with the cancer cells presenting a native peptide from which said analogue segment is derived such that the human cytotoxic T cells are capable of producing a heteroclitic immune response against the cancer cells.

In this embodiment the method further comprises providing a DNA encoding the synthetic peptide and expressing the DNA. The DNA may be inserted into a suitable vector. Alternatively, the DNA may be inserted into an antigen-presenting cell. An example of an antigen-presenting cell is a dendritic cell.

In one aspect of this embodiment the human immune cells are contacted in vivo in an individual having a cancer. In a related aspect the human immune cells are contacted in vivo in a donor and the method further comprises obtaining the cytotoxic T cells from the donor and infusing the cytotoxic T cells into a recipient having a cancer.

In another aspect the cells are contacted ex vivo and the method further comprises obtaining the human immune cells from a donor prior to the contacting the human immune cells with the pharmaceutical composition and infusing the activated immune cells into an individual having a cancer prior to the inducing formation and proliferation of cytotoxic T cells. In a related aspect the cells are contacted ex vivo and the method further comprises obtaining human immune cells from a donor prior to contacting the human immune cells. In this aspect, both contacting the human immune cells and formation and proliferation of the cytotoxic T-cells occurs ex vivo, infusing the cytotoxic T-cells into an individual having a cancer.

In all aspects of this embodiment, representative human immune cells may be peripheral blood mononuclear cells, bone marrow cells, dendritic cells, or macrophages. The synthetic peptides and analogue segments comprising the synthetic peptides are as described supra. In aspects of this embodiment the analogue segments comprising the synthetic peptide may be derived from a native p210-b3a2 peptide, a native p210-b2a2 peptide, a native p190-e1a2 peptide or from a native WT-1 peptide as described supra. Furthermore, the amino acid sequences of these synthetic peptides or the analogue segments comprising the synthetic peptides may have an amino acid sequence as identified supra for p210-b3a2-, p210-b2a2- or WT-1-derived analogues.

In a related aspect WT-1 analogue segments and p210-b3a2 and p210-b2a2 derived analogue segments may induce a heteroclitic response against leukemic cells. Representative leukemic cells are chronic myelogenous leukemic cells. In another related aspect WT-1 analogue segments may induce a heteroclitic response against from breast cancer, lymphoma, mesothelioma, lung cancer, testicular cancer, or ovarian cancer.

In yet another embodiment of the present invention there is provided a method of treating a cancer in a human, comprising administering the pharmaceutical compositions described herein to the human; and inducing a heteroclitic response by cytotoxic T-cells that recognize at least the analogue segment of said synthetic peptide against cancer cells presenting a native peptide from which said analogue segment is derived, said cytotoxic T-cells recognizing or killing said cancer cells thereby treating the cancer.

The synthetic peptides or DNAs encoding the synthetic peptides are as described supra. In aspects of this embodiment the analogue segment comprising the synthetic peptides may be derived from a native p190 e1a2 peptide, a native p210-b3a2 peptide, a native p210-b2a2 peptide, or from a native WT-1 peptide as described supra. Furthermore, the amino acid sequences of these synthetic peptide or the analogue segments comprising the synthetic peptides are as identified supra for p210-b3a2-, p210-b2a2- or WT-1-derived analogue segments.

In one aspect WT-1 at least the analogue segments comprising the synthetic peptides and p210-b3a2 and p210-b2a2 derived synthetic peptides may treat a leukemia. A representative leukemia is chronic myelogenous leukemic. In another aspect WT-1 at least the analogue segments comprising the synthetic peptides may treat breast cancer, lymphoma, mesothelioma, lung cancer, testicular cancer, or ovarian cancer.

In a related embodiment, there is provided a method of inducing a heteroclitic immune response in a human, comprising administering to the human an effective amount of the immunogenic compositions described supra; activating human immune cells with the immunogenic composition; and inducing formation and proliferation of human cytotoxic T cells against the activated cells presenting at least the analogue segment of the synthetic peptide comprising the immunogenic composition. In this method, the human cytotoxic T cells will cross-react with a cell comprising a cancer presenting a native peptide from which said analogue segment is derived, thereby inducing the heteroclitic immune response.

In one aspect of this embodiment, the human may have an active cancer, may be in remission from cancer or may be at risk of developing a cancer. In an alternative aspect of this embodiment human donates the cytotoxic T-cells to an individual having an active cancer, is in remission from cancer or is at risk of developing a cancer.

In aspects of this embodiment, the immunogenic compositions, the human immune cells and the synthetic peptides and the analogue segments comprising the synthetic peptides are as described supra. In one aspect at least WT-1 analogue segments and p210-b3a2 and p210-b2a2 derived analogue segment comprising synthetic peptides may induce a heteroclitic response in the human against leukemia. A representative leukemia is chronic myelogenous leukemic. In another aspect at least WT-1 analogue segments may induce a heteroclitic response in the human against breast cancer, lymphoma, mesothelioma, lung cancer, testicular cancer, or ovarian cancer.

Provided herein are synthetic immunogenic peptides with an amino acid sequence containing at least an analogue segment of a native peptide that demonstrates improved binding over the native peptides to HLA A0201 or to HLA A0301 complexes. These synthetic peptides or analogue segments can stimulate T-cells to cross-react with the native peptides thus eliciting a heteroclitic immune response that will recognize or kill cells presenting the native peptides. Such cells are characteristic of a pathophysiological state, for example, but not limited to, a cancer. At least the analogue segments comprising the synthetic peptides will bind with more affinity to the HLA class I and class II molecules that are instrumental in presenting the analogue segments to the T-cells than the native peptide itself.

The synthetic peptide analogue segments are designed by making one or two amino acid substitutions in anchor or auxiliary residues. Although the native peptides particularly described herein are nonamers encompassing the anchor or auxiliary residues, analogues may be designed having about 70% to about 130% of the amino acids in the native peptide. In the instant invention the synthetic peptide analogues may have about 8-12 amino acids. Such substitutions are determined by a bioinformatic model system (BIMAS) which uses a matrix approach to predict binding and ranks the peptides based on predicted binding to the HLA molecule. The amino acid sequences and predicted score for binding to HLA A0201 and HLA A0301 are generated by online software BIMAS available at http://bimas.dcrt.nih.gov/cgi-bin/molbio/ken parker comboform and SYFPEITHI available at http://syfpeithi.bmi-heidelberg.com/.

The synthetic peptide may be a precursor to the analogue segment which may be a degradation product of the synthetic peptide. Such precursor may be a bcr-able fusion protein such that the synthetic analogue spans the breakpoint region of the fusion protein. Alternatively, the precursor may be a WT1 protein such that the analogue segments replaces a native peptide sequence within WT1.

Additionally, the synthetic peptide is or comprises analogue segments that may be analogues of the breakpoint region of the bcr-abl fusion protein, which is the oncogenic protein required for neoplasia in chronic myelogenous leukemia. The synthetic peptides are or comprise analogue segments derived from the junctional sequences of p210-b3a2, p210-b2a2 and p190-e1a2. More preferably, the synthetic peptides or the analogue segments are derived from p210-b3a2 and p210-b2a2 in which single or double amino acid substitutions were introduced into the peptides at key HLA A0201 binding positions. These high affinity peptide analogues were able to generate specific CD8+ T cells far more efficiently than the native peptides and are capable of stimulating human CD8+ CTL heteroclitic responses that cross-react with the native sequences presented on leukemic cells.

Preferred synthetic peptides or analogue segments are the p210-b3a2 analogues p210C, p210D, p210E, and p210F, more preferably p210C, and the p210-b2a2 analogues b2a2 A3, b2a2 A4 and b2a2 A5, more preferably b2a2 A3. Table 1 shows the amino acid sequences and binding predictions of native and synthetic analogues. The underlined K in the b3a2 and underlined blue E in b2a2 are the amino acids in the breakpoint. Highlighted residues represent modifications from the native sequence.

TABLE 1

HLA 0201 native peptides of ber-abl fusion protein and synthetic peptide analogues

| Name | Native sequence | Analogue sequence | BIMAS score |
|---|---|---|---|
| CMLA2 | SSKALQRPV SEQ ID NO: 1 | | 0.003 |
| p210F | | YLKALQRPV SEQ ID NO: 2 | 2.240 |
| CMLA3 | KQSSKALQR SEQ ID NO: 3 | | 0.005 |
| p210A | | KQSSKALQV SEQ ID NO: 4 | 24.681 |
| p210B | | KLSSKALQV SEQ ID NO: 5 | 243.432 |
| p210Cn | KALQRPVAS SEQ ID NO: 6 | | 0.013 |
| p210C | | KLLQRPVAV SEQ ID NO: 7 | 900.689 |
| p210Dn | TGFKQSSKA SEQ ID NO: 8 | | 0.120 |
| p210D | | TLFKQSSKV SEQ ID NO: 9 | 257.342 |
| p210E | | YLFKQSSKV SEQ ID NO: 10 | 1183.775 |
| b3a2A | LTINKEEAL SEQ ID NO: 11 | | 0.247 |
| b3a2 A1 | | LLINKEEAL SEQ ID NO: 12 | 17.795 |
| b3a2 A2 | | LTINKVEAL SEQ ID NO: 13 | 21.996 |
| b3a2 A3 | | YLINKEEAL SEQ ID NO: 14 | 48.151 |
| b3a2 A4 | | YLINKEEAV SEQ ID NO: 15 | 156.770 |
| b3a2 A5 | | YLINKVEAL SEQ ID NO: 16 | 110.747 |

The synthetic immunogenic peptides may be analogue segments or comprise analogue segments derived from WT1 protein. Computer prediction analysis, as described herein, predicted synthetic peptides analogues derived from nonamer sequences of the WT1 protein in which single amino-acid substitutions were introduced at HLA A0201 binding and single or double amino acid substitutions were introduced at A0301 binding positions. These synthetic peptide analogues or analogue segments were able to generate specific CD8+ or CD3+ T cells far more efficiently than the native peptides and are capable of stimulating human CD8+ or CD3+ CTL heteroclitic responses that cross-react with the native sequences presented on leukemic cells or on other cells that present these native WT-1 peptides. Tables 2 and 3 show the amino acid sequences and binding predictions of native WT-1 and synthetic WT-1 peptide analogues. Highlighted residues represent modifications from the native sequence.

TABLE 2

HLA 0201 native peptides from WT-1 and synthetic analogues

| Name | Native sequence | Analogue sequence | BIMAS score |
|---|---|---|---|
| WT-1A | RMFPNAPYL SEQ ID NO: 17 | | 313 |
| WT-1 A1 | | YMFPNAPYL SEQ ID NO: 18 | 1444 |
| WT-1 B | SLGEQQYSV SEQ ID NO: 19 | | 285 |
| WT-1 B1 | | YLGEQQYSV SEQ ID NO: 20 | 1311 |
| WT-1 C | ALLPAVPSL SEQ ID NO: 21 | | 181 |
| WT-1 C1 | | YLLPAVPSL SEQ ID NO: 22 | 836 |
| WT-1 D | NLGATLKGV SEQ ID NO: 23 | | 159 |
| WT-1 D1 | | YLGATLKGV SEQ ID NO: 24 | 735 |
| WT-1 E | DLNALLPAV SEQ ID NO: 25 | | 11 |
| WT-1 E1 | | YLNALLPAV SEQ ID NO: 26 | 735 |
| WT-1 F | GVFRGIQDV SEQ ID NO: 27 | | 51 |
| WT-1 F1 | | GLRRGIQDV SEQ ID NO: 28 | 591 |
| WT-1 G | KRYFKLSHL SEQ ID NO: 29 | | 1 |
| WT-1 G1 | | KLYFKLSHL SEQ ID NO: 30 | 550 |
| WT-1 H | ALLLRTPYS SEQ ID NO: 31 | | 1 |
| WT-1 H1 | | ALLLRTPYV SEQ ID NO: 32 | 1415 |
| WT-1 J | CMTWNQMNL SEQ ID NO: 33 | | 15 |

TABLE 2-continued

HLA 0201 native peptides from WT-1 and synthetic analogues

| Name | Native sequence | Analogue sequence | BIMAS score |
|---|---|---|---|
| WT-1 J1 | | YMTWNQMNL SEQ ID NO: 34 | 70 |

TABLE 3

HLA 0201 native peptides from WT-1 and synthetic analogues

| Name | Native sequence | Analogue sequence | BIMAS score |
|---|---|---|---|
| A3WT-1 A | NMHQRNMTK SEQ ID NO: 35 | | 40 |
| A3WT-1 A1 | | NMYQRNMTK SEQ ID NO: 36 | 200 |
| A3WT-1 A2 | | NMHQRVMTK SEQ ID NO: 37 | 120 |
| A3WT-1 A3 | | NMYQRVMTK SEQ ID NO: 38 | 600 |
| A3WT-1 B | QMNLGATLK SEQ ID NO: 39 | | 20 |
| A3WT-1 B1 | | QMYLGATLK SEQ ID NO: 40 | 100 |
| A3WT-1 B2 | | QMNLGVTLK SEQ ID NO: 41 | 60 |
| A3WT-1 B3 | | QMYLGVTLK SEQ ID NO: 42 | 300 |
| A3WT-1 C | FMCAYPGCNK SEQ ID NO: 43 | | 30 |
| A3WT-1 C1 | | FMYAYPGCNK SEQ ID NO: 44 | 150 |
| A3WT-1 C2 | | FMCAYPFCNK SEQ ID NO: 45 | 90 |
| A3WT-1 C3 | | FMYAYPFCNK SEQ ID NO: 46 | 450 |
| A3WT-1 D | KLSHLQMHSR SEQ ID NO: 47 | | 18 |
| A3WT-1 D1 | | KLYHLQMHSR SEQ ID NO: 48 | 90 |
| A3WT-1 D2 | | KLSHLQMHSK SEQ ID NO: 49 | 90 |
| A3WT-1 D3 | | KLYHLQMHSK SEQ ID NO: 50 | 450 |

The present invention also provides a pharmaceutical composition of a therapeutic amount of the synthetic peptides or analogue segments or a genetic sequence or DNA encoding the same and a pharmaceutical carrier, as is known in the art. The pharmaceutical composition may be formulated with the pharmaceutical carrier for administration by any of the many techniques known to those of skill in the art. For example, the pharmaceutical composition may be administered parenterally, intravenously, subcutaneously, intradermally, intramucosally, topically, orally, or by inhalation.

Therefore, it is contemplated that the synthetic peptides or analogue segments or pharmaceutical compositions thereof may be used in the preparation of an immunogenic composition suitable to effect immunization of a subject. The immunogenic composition may comprise a carrier or a suitable adjuvant to boost immune response or a combination thereof, as are known in the art. The immunogenic composition further may comprise a diluent standard in the art as described herein. The immunogenic composition may comprise a vaccine.

A carrier may comprise one or more proteins or peptides. Examples of carriers are well known and may be, although not limited to keyhole limpet hemocyanin, an albumin, such as human serum albumin or a polyamino acid. Additionally, a carrier may comprise a live antigen-presenting cell, such as a dendritic cell, which presents the synthetic peptides described herein. A suitable adjuvant may be Freund's adjuvant, aluminum phosphate, aluminum hydroxide, alum, QS21, BCG. These compositions further may comprise a physiologically acceptable diluent, e.g., water, phosphate buffered saline or saline.

Additionally, a genetic sequence encoding a synthetic peptide or an analogue segment thereof may be delivered as naked DNA to an individual via appropriate methods known in the art. Alternatively, the genetic sequence may be introduced or inserted into a suitable vector, such as for example, but not limited to, attenuated viral or bacterial vectors, as are standard in the art. Furthermore, the naked DNA or vectors comprising the genetic sequence or DNA may be transduced into an antigen-presenting cell, e.g., a dendritic cell. The genetic sequence, DNA, vector or transduced antigen-presenting cell may be introduced into an individual in need of the treatment or into a healthy donor whereupon the DNA encoding the genetic sequence expresses the synthetic peptide to elicit a cytotoxic T-cell response. Donor T-cells may then be infused into a patient in need thereof.

The pharmaceutical or immunogenic compositions may be used to treat a disease or a condition such as cancer. Administration of the synthetic peptides or analogue segments comprising the pharmaceutical compositions induces a heteroclitic response against native peptides expressed on the cancer cells thereby effecting a therapeutic result. Native peptides of the breakpoint region of bcr-abl proteins and native peptides of WT-1 protein are expressed on leukemic cells in chronic myelogenous leukemia. Native WT-1 peptides are expressed on other leukemic cells and, additionally, on cancerous cells of different solid tumors. Such cancers may be, although not limited to, breast, lymphoma, mesothelioma, lung, testicular, or ovarian cancers.

It is contemplated that the synthetic peptides or synthetic analogue segments thereof or genetic sequences encoding the same or the pharmaceutical or the immunogenic compositions thereof can induce human cytotoxic T cells to produce a heteroclitic immune response against cancerous cells, for example, leukemic cells. Contacting human immune cells with at least the analogue segment that is or comprises the synthetic peptides activates the immune cells to induce formation and proliferation of human cytotoxic T cells that will recognize or react against a cell presenting the synthetic peptide. Such cytotoxic T cells cross react with human cells presenting the native peptides from which the analogue segment is derived thereby producing a heteroclitic response.

One of ordinary skill in this art would recognize the word "contacting" in terms of activating target immune cells to elicit a subsequent immune response as referring to any suitable delivery method of bringing an immunogenic agent into contact with the target cells. In vitro or ex vivo this is achieved by exposing the target cells to the agent in a suitable medium. For in vivo applications, any known method of administration is suitable as described herein.

Thus, the synthetic peptides or analogue segments thereof described herein may be used to activate T-cells ex vivo or in vivo. In vivo, the synthetic peptides or analogue segments thereof or DNA encoding the same may be administered to a patient or to a healthy donor to induce cytotoxic T-cells. If administered to a donor these cytotoxic T-cells are obtained from the donor and infused into an individual in need of them, such as an individual with an active cancer, in remission from a cancer or at risk for developing a cancer.

Ex vivo, the T cells are obtained from a patient or from a healthy donor and are incubated in the presence of antigen presenting cells and a synthetic peptide or at least an analogue segment thereof to activate the T-cells. The activated T-cells subsequently are infused back into the patient where they will recognize and/or destroy cells presenting the native peptide. Alternatively, human immune cells may be incubated with the synthetic peptide or at least an analogue segment thereof whereupon the activated immune cells are infused back into the patient to induce T-cell production against both the activated cells and cell presenting the native peptide. Examples of immune cells may be peripheral blood mononuclear monocytic cells, bone marrow cells, dendritic cells, or macrophages.

It is contemplated further that administration of the synthetic peptide or at least an analogue segment thereof or pharmaceutical compositions thereof induces an immune response in a subject, preferably, although not limited to, a CD8/HLA A or CD3/HLA A class I immune response. As such, the synthetic peptides or at least an analogue segment thereof may be used in a method of immunizing a subject against a pathophysiologic condition or disease presenting HLA molecules, e.g., a leukemia, such as chronic myelogenous leukemia. Additionally, WT-1 synthetic peptides or at least analogue segments thereof may be used to induce an immune response in a subject with other leukemias or cancers such as, although not limited to, breast, lymphoma, mesothelioma, lung, testicular, or ovarian cancers. As used herein, immunizing or immunization of a subject encompasses full and partial immunization whereby the subject becomes fully immune to the condition or partially immune to the condition. The subject may be a mammal, preferably a human.

The subject may have a condition or disease which may be active or in remission, prior to immunization. Alternatively, if at risk for developing the disease or condition, the subject may be immunized prior to such development. One of ordinary skill in the art would be able to assess the risk factors, such as environmental risk factors or personal risk factors, such as family history, genetic makeup or behavior, to make a determination of risk in the subject.

The pharmaceutical compositions and immunogenic compositions may be administered one or more times to achieve a therapeutic or an immunogenic effect. It is well within the skill of an artisan to determine dosage or whether a suitable dosage comprises a single administered dose or multiple administered doses. An appropriate dosage depends on the subject's health, the progression or remission of the disease, the route of administration and the formulation used.

The following examples are given for the purpose of illustrating various embodiments of the invention and are not meant to limit the present invention in any fashion.

EXAMPLE 1

Synthetic Peptides

Each of the peptides utilized in this study was purchased and was synthesized by Genemed Synthesis Inc, CA using fluorenylmethoxycarbonyl chemistry, solid phase synthesis and purified by high pressure liquid chromatography. The quality of the peptides was assessed by high-performance liquid chromatography analysis and the expected molecular weight was observed using matrix-assisted laser desorption mass spectrometry. Peptides were sterile and >90% pure. The peptides were dissolved in DMSO and diluted in phosphate-buffered saline (PBS) at pH 7.4 or saline to give a concentration of 5 mg/ml and were stored at −80° C. For in vitro experiments an irrelevant control peptide, HLA A24 consensus, was used.

EXAMPLE 2

Cell Lines

Cell lines were cultured in RPMI 1640 medium supplemented with 5% FCS, penicillin, streptomycin, 2 mM glutamine and 2-mercaptoethanol at 37° C. in humidifier air containing 5% CO2. SKLY-16 is a human B cell lymphoma expressing HLA A0201 and T2 is a human cell line lacking TAP1 and TAP2 and therefore unable to present peptides derived from cytosolic proteins.

EXAMPLE 3

T2 Assay for Peptide Binding and Stabilization of HLA A0201 Molecules

T2 cells (TAP−, HLA-A0201 +) were incubated overnight at 27° C. at 1×10E6 cells/ml in FCS-free RPMI medium supplemented with 5 µg/ml human β2 m (Sigma, St Louis, Mo.) in the absence, i.e., negative control, or presence of either a positive reference tyrosinase peptide or test peptides at various final concentrations of 50, 10, 1, and 0.1 µg/ml. Following a 4 h incubation with 5 µg/ml brefeldin A (Sigma), T2 cells were labeled for 30 min at 4° C. with a saturating concentration of anti-HLA-A2.1 (BB7.2) mAb, then washed twice. The cells then were incubated for 30 min at 4° C. with a saturating concentration of FITC-conjugated goat IgG F(ab')2 anti-mouse Ig (Caltag, South San Francisco, Calif.), washed twice, fixed in PBS/1% paraformaldehyde and analyzed using a FACS Calibur cytofluorometer (Becton Dickinson, Immunocytometry systems, San Jose, Calif.).

The mean intensity of fluorescence (MIF) observed for each peptide concentration, after subtraction of the MIF observed without peptide, was used as an estimate of peptide binding. Stabilization assays were performed similarly. Following initial evaluation of peptide binding at time 0, cells were washed in RPMI complete medium to remove free peptides and incubated in the continuous presence of 0.5 µg/ml brefeldin-A for 2, 4, 6, and 8 hours. The amount of stable peptide-HLA-A2.1 complexes was estimated as described above by indirect immunofluorescence analysis. The half time of complexes is an estimate of the time required for a 50% reduction of the time 0 mean intensity of fluorescence value.

EXAMPLE 4

Competition Radioimmunoassay

Target cells were washed two times in PBS with 1% bovine serum albumin (Fisher Chemicals, Fairlawn, N.J.). Cells were resuspended at $10^7$/ml on ice and the native cell surface bound peptides were stripped for 2 minutes at 0° C. using citrate-phosphate buffer in the presence of beta$_2$ microglobulin 3 mg/ml. The pellet was resuspended at 5 to $10 \times 10^6$ cells/ml in PBS/1% BSA in the presence of 3 mg/ml beta$_2$ microglobulin and 30 mg/ml deoxyribonuclease and 200 ml aliquots were incubated with HLA-specific peptides for 10 min at 20° C.

Binding of $^{125}$I-labeled peptide with or without competitive unlabeled peptide was done for 30 min at 20° C. Total bound $^{125}$I was determined after two washes using PBS/2% BSA and one wash with PBS. Relative affinities were determined by comparison of escalating concentrations of the test peptide versus a known binding peptide. Peptides of affinities <500 nM were chosen for use.

A specificity analysis of the binding of peptide to HLA on the live cell surface (SKLY-16) was conducted to confirm that the binding was to the appropriate HLA molecule and to characterize its restriction. This included competition with excess unlabeled peptides known to bind to the same or disparate HLA molecules and use of target cells which expressed the same or disparate HLA types. This assay was performed on live fresh or 0.25% paraformaldehyde-fixed human peripheral blood mononuclear cells (PBMC), leukemia cell lines and EBV-transformed T-cell lines of specific HLA types. The relative avidity of the peptides found to bind MHC molecules on the specific cells were assayed by competition assays as described above against $^{125}$I-labeled peptides of known high affinity for the relevant HLA molecule, e.g., tyrosinase or HBV peptide sequence.

EXAMPLE 5

In vitro Immunization and Human T Cell Cultures

After informed consent, peripheral blood mononuclear cells from HLA-A0201 positive healthy donors and chronic myeloid leukemia patients were obtained by Ficoll-density centrifugation. Peripheral blood dendritic cells (DCs) were generated as follows: Monocyte-enriched peripheral blood mononuclear cell fractions were isolated, using a plastic adherence technique, from total peripheral blood mononuclear cells. The plastic-adherent cells were cultured further in RPMI 1640 medium supplemented with 1-5% autologous plasma, 1000 U/mL recombinant human interleukin (IL)-4 (Shering-Plough, N.J.), and 1000 U/mL recombinant human granulocyte-macrophage colony-stimulating factor (GM-CSF) (Immunex, Seattle).

On days 2 and 4 of incubation, part of the medium was exchanged for fresh culture medium supplemented with IL-4 and GM-CSF and culture was continued. On day 6, half of the medium was exchanged for culture medium supplemented with IL-4, GM-CSF, and 10 ng/mL recombinant human tumor necrosis factor (TNF)-alpha (R&D system) and 500 ng/ml of trimeric soluble CD40L (Immunex, Seattle). On day 9, the cells were harvested and used as monocyte-derived dendritic cells for antigen stimulation. The cells generated expressed dendritic cell-associated antigens, such as CD80, CD83, CD86, and HLA class I and class II on their cell surfaces (data not shown).

T lymphocytes were isolated from the same donors by use of negative selection by depletion with an anti-CD11b, anti- CD56 and CD19 monoclonal antibody (Miltenyi, Calif.). A total of 1×10E6 of pure T lymphocytes were cultured with 1×10E5 autologous dendritic cells in RPMI 1640 medium supplemented with 5% heat-inactivated human autologous plasma with bcr-abl synthetic peptides at a concentration of 10 µg/mL and b2 microglobulin at 2 µg/ml in a 24 well plates in the presence of 5-10 ng/mL recombinant human IL-7 (Genzyme) and 0.1 ng/ml of IL-12.

After culture for 3 days 20 U/ml of IL-2 was added. After 10 days, 1×10E6 cells were stimulated again by adding 2×10e5 autologous magnetically isolated CD14+ monocytes together with 10 ng/ml of IL-7 and 20 U/ml of IL-2 and peptide at a concentration of 10 µg/mL. In some cases, after culture for another 7 days, the cells were stimulated a third time in the same manner. After the second or third stimulation, CD8 T cells were isolated magnetically and cytotoxicity and gamma-IFN secretion of these cells were examined.

EXAMPLE 6

Gamma Interferon ELISPOT

HA-Multiscreen plates (Millipore, Burlington, Mass.) were coated with 100 µl of mouse-anti-human IFN-gamma antibody (10 µg/ml; clone 1-D1K, Mabtech, Sweden) in PBS, incubated overnight at 4° C., washed with PBS to remove unbound antibody and blocked with RPMI/autologous plasma for 1 h at 37° C. Purified CD8+ T cells, more than 95% pure, were plated at a concentration of $1\times10^5$/well. T cells were stimulated with 1×10E4 T2 cells per well, pulsed with 10 µg/ml of β2-microglobulin (Sigma, St. Louis) and either 50 µg/ml of test peptide, positive control influenza matrix peptide, or irrelevant control peptide at a final volume of 100-200 µl/well. Control wells contained T2 cells with or without CD8+ cells. Additional controls included medium or CD8+ alone plus PBS/5% DMSO diluted according to the concentrations of peptides used for pulsing T2 cells.

After incubation for 20 hours at 37° C., plates were washed extensively with PBS/0.05% Tween and 100 µl/well biotinylated detection antibody against human IFN-g at 2 µg/ml (clone 7-B6-1, Mabtech, Sweden) were added. Plates were incubated for an additional 2 hours at 37° C. and spot development was performed. Spot numbers were automatically determined with the use of a computer-assisted video image analyzer with KS ELISPOT 4.0 software (Carl Zeiss Vision, Germany).

EXAMPLE 7

Cytotoxicity Assay

The presence of specific CTLs was measured in a standard 4 h-chromium release assay. 4×10E6 targets were labeled with 300 µCi of $Na_2{}^{51}CrO_4$ (NEN Life Science Products, Inc. Boston, Mass.) for 1 hour at 37° C. After washing, cells at 2×10E6/ml were incubated with or without synthetic peptides at a concentration of 10 µg/ml for 2 hours at 20° C. in presence of $\beta_2$microglobulin at 3 µg/ml. After washing by centrifugation, target cells were resuspended in complete media at 5×10E4 cells per ml and plated in a 96 well U-bottom plate (Becton Dickinson®, N.Y.) at 5×10E3 cells per well with effector cells at effector to target ratios (E/T) ranging from 100:1 to 10:1. Plates were incubated for 5 hours at 37 C. in 5% $CO_2$.

Supernatant fluids were harvested and radioactivity was measured in a gamma counter. Percent specific lysis was determined from the following formula: 100×[(experimental release minus spontaneous release)/(maximum release minus spontaneous release)]. Maximum release was determined by lysis of targets in 2.5% Triton X-100.

EXAMPLE 8

Identification and Generation of Peptides with a High Probability to Bind to HLA 0201

Amino acid sequences of the human b3a2 and b2a2 fusion proteins were scanned for peptides with potential binding capacity for HLA A0201, a subtype encompassing 95% of the HLA-A02 allele. HLA-A0201 is expressed in about 40% of the Caucasian population. No peptides with high or intermediate affinity were identified in the native b3a2 or b2a2 fusion proteins with > than 1 minute of predicted half life. One peptide that does not exhibit the consensus HLA 0201 binding motifs has been described but it has weak avidity to MHC.

Based on this information and by using the software of the Bioinformatics & Molecular Analysis Section (National Institutes of Health, Washington, D.C.) available at http://bimas.dcrt.nih.gov/cgi-bin/molbio/ken_parker_comboform. This software ranks 9-mer or 10-mer peptides on a predicted half-time dissociation coefficient from HLA class I molecules (Pinilla, et al. Curr Opin Immunol, 11(2): p. 193-202 (1999)). Analogue peptides were designed by changing one or both anchor amino acids or additional amino acids adjacent to anchor amino acids. Single or double amino acid substitutions were introduced at HLA A0201 preferred residues at positions 1, 2, 6 and 9 (Table 1) to yield sequences that had comparatively high binding scores predicted for HLA A0201 molecules.

The predicted half life for binding to HLA A0201 was greater than 240 minutes in four synthetic peptides and less than 240 in seven. All the native peptides were predicted to have less than an hour of half life. Most of the substitutions affected the primary or secondary anchor motifs, i.e., leucine in position 2 or valine in position 9 or position 6, but in some cases, a tyrosine was substituted in position 1. This substitution has been shown to stabilize the binding of position 2 anchor residue.

EXAMPLE 9

Binding of HLA-A0201 by Synthetic Peptides Analogues of b2a2 and b3a2 Native Peptides The immunogenicity of MHC class I-restricted peptides requires the capacity to bind and stabilize MHC class I molecules on the live cell surface. Moreover the computer prediction models above have only 60-80% predictive accuracy. Direct measurement of the strength of the interaction between the peptides and the HLA-A0201 molecule was made using a conventional binding and stabilization assay that uses the antigen-transporting deficient (TAP2-) HLA-A0201 human T2 cells. T2 cells lack TAP function and consequently are defective in properly loading class I molecules with antigenic peptides generated in the cytosol. The association of exogenously added peptides with thermolabile, empty HLA-A2 molecules stabilizes them and results in an increase in the level of surface HLA-A0201 recognizable by specific mAb such as BB7.2.

Figure 1B:
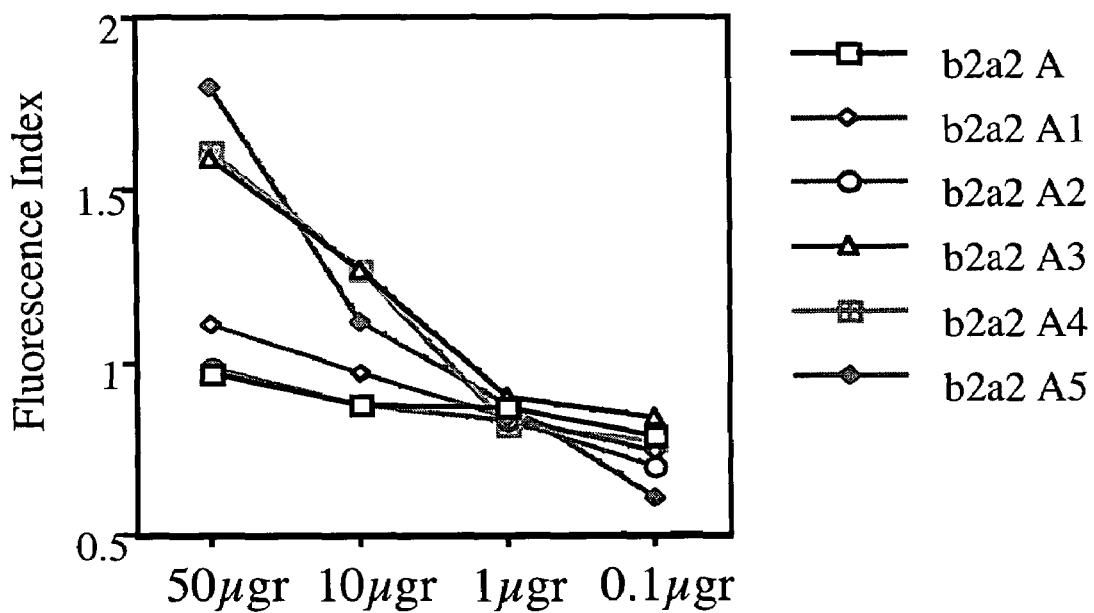

Seven out of the eleven peptides designed to have higher binding scores exhibited a relatively high binding affinity for HLA A0201 molecules as measured by the T2 assay (FIGS. 1A-1B). A rough correlation between binding scores and binding affinity was established, thus indicating the partial utility of the computer generated binding scores for predicting peptides that will bind to MHC class I molecules on live cells. Some of these peptides demonstrated the same order of binding affinity as that of viral antigen such as influenza, which are among the most potent known antigens for CTL induction. In four cases a good correlation between computer predicted half-life and T2 stabilization was not found.

One of the peptides derived from b3a2, p210C, was mutated from a peptide that did not have a good prediction score. However, the native sequence is able to bind HLA A0201 weakly and at the same level that the previously described CMLA2 peptide. To design p210C, a neutral alanine in position two was substituted by a leucine and a serine in position nine was substituted by a valine. p210C has a high BIMAS score that correlated with T2 binding assay data (FIG. 1A).

p210F is a peptide derived from the sequence previously described by Yotonda et al. CMLA2, shown to be a weak binder in the T2 assay. In p210F the two serines in position one and two were substituted by a tyrosine and a leucine. The BIMAS prediction showed a 700 fold improvement and the binding to T2 cell revealed an excellent avidity for HLA A0201 molecules (FIG. 1A).

Of the peptides derived from b2a2, all were generated from a peptide that not predict a good binding to HLA A0201. Three peptides, b2a2 A3-A5 (Table 1) bound well to HLA A0201 molecules (FIG. 1B). These three peptides have a tyrosine-leucine sequence substitution at position 1 and 2 and also a valine substitution in position 6 or 9.

EXAMPLE 10

Assessment of the Dissociation Time of b2a2 and b3a2 Synthetic Peptides Analogues from HLA A0201

The immunogenicity of peptide antigens depends on a low dissociation rate of MHC/peptide complexes. The stability of complexes formed between HLA-A0201 and the b3a2 analogue peptides was assayed on T2 cells over time. Overnight incubation of T2 cells with saturating amounts of HLA-A0201 binding peptides and human $\beta2$ microglobulin resulted in increased surface expression of HLA-A0201 molecules. After peptide removal and addition of Brefeldin A to inhibit protein synthesis, T2 cells were incubated at 37° C. and the amount of HLA-A0201 molecules remaining at the cell surface was determined after various incubation times.

The stability of each peptide/HLA-A0201 complex was then normalized relative to that observed for the tyrosinase D peptide or HIV gag peptide which are peptides with known high affinity and half life. HLA-A0201 complexes formed with peptides p210A and p210B were unstable, reaching background levels in less than 1 h of incubation at 37° C. In contrast, peptides p210C, p210D, p210E and p210F formed complexes that were relatively stable over 6-8 hours.

EXAMPLE 11

Induction of CD8 Immune Response Against b2a2 and b3a2 Synthetic Peptide Analogues While affinity for MHC molecules is necessary for peptide immunogenicity, there is also a requirement for presence of reactive precursor T cells with appropriate T cell receptors. Using an optimized T cell-expansion system, with monocyte derived DC, CD14+ cells as APC, and purified T cells, the ability of the synthetic b3a2 and b2a2 analogues to stimulate peptide-specific CTLs is examined. Ten healthy HLA A0201 donors as well 5 patients with CML were studied.

Figure 2A:
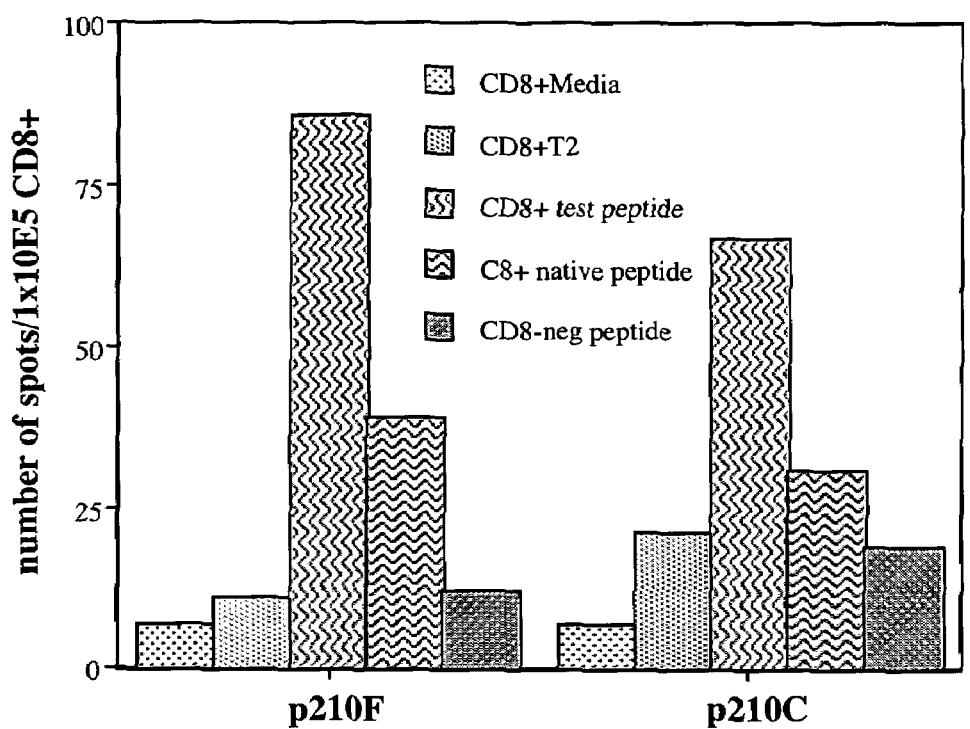
FIGS. 2A-2B show the results of a CD8+ gamma interferon ELISPOT from a healthy HLA A0201 donor (FIG. 2A) using p210C and p210F peptides and from a CML patient in chronic phase HLA A0201 (FIG. 2B) using the p210C peptide.

Five out of the ten individuals responded to immunization, generating T cells that secreted IFN gamma when challenged with different peptide-pulsed T2 cells as targets. p210D and p210E produced an immune response in some of the donors tested although p210C and p210F generated a more consistent and higher immune-responses (FIG. 2A). Responses were observed after the second or third round of peptide stimulation after CD8+ isolation or in unpurified CD3+ T cells.

The spot numbers were consistently higher with peptides that bound with higher affinity to HLA 0201 molecules as determined by T2 assay. More importantly, T cells generated in the presence of the new synthetic analogues were able to recognize the native sequences. p210C and p210F were able to stimulate T cells to recognize their respective native sequences (FIG. 2A). CML A2, the native sequence from p210F is a natural weak binder and there is indirect evidence that it can be naturally expressed in the surface of chronic myelogenous leukemia blasts. No immune response could be generated against the p210A and p210B, despite attempts using different donors. This result is consistent with their reduced affinity for MHC.

Figure 2B:
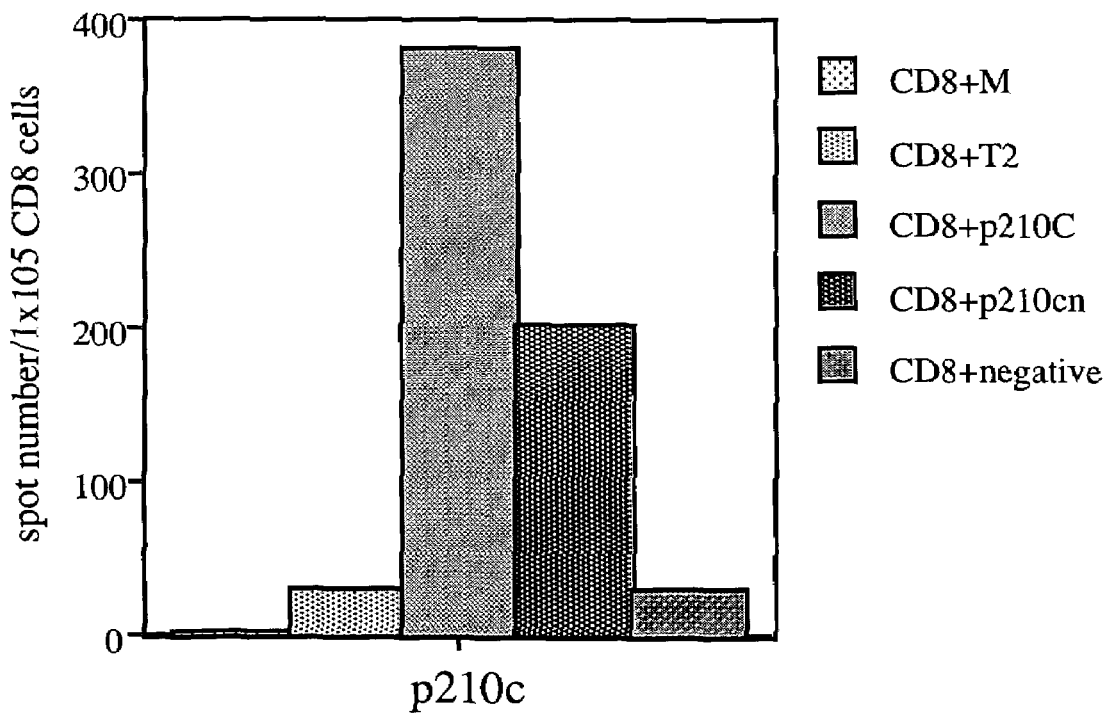

A chronic myelogenous leukemia patient in chronic phase HLA A0201 responded to p210C stimulation of T cells and demonstrated T-cell cross-reactivity with native p210cn peptide. Response was observed after the second round of T-cell stimulation in vitro (FIG. 2B).

The peptides derived from b2a2 also generated a significant immune response as measured by gamma interferon secretion CD3+ T cells. Peptides b2a2A3, A4 and A5 generated an immune response in two healthy donors (FIG. 3A). The response against b2a2 A3 was more consistent between donors. T cells generated in the presence of b2a2 A3 were able to identify the original native sequence. This is of special relevance because the native sequence is a weak/intermediate binder to HLA. Again, a CML patient in chronic phase HLA A0201 responded to b2a2 A3 stimulation of T cells and demonstrated T-cell cross-reactivity with native b2a2 A peptide (FIG. 3B).

Figure 4A:
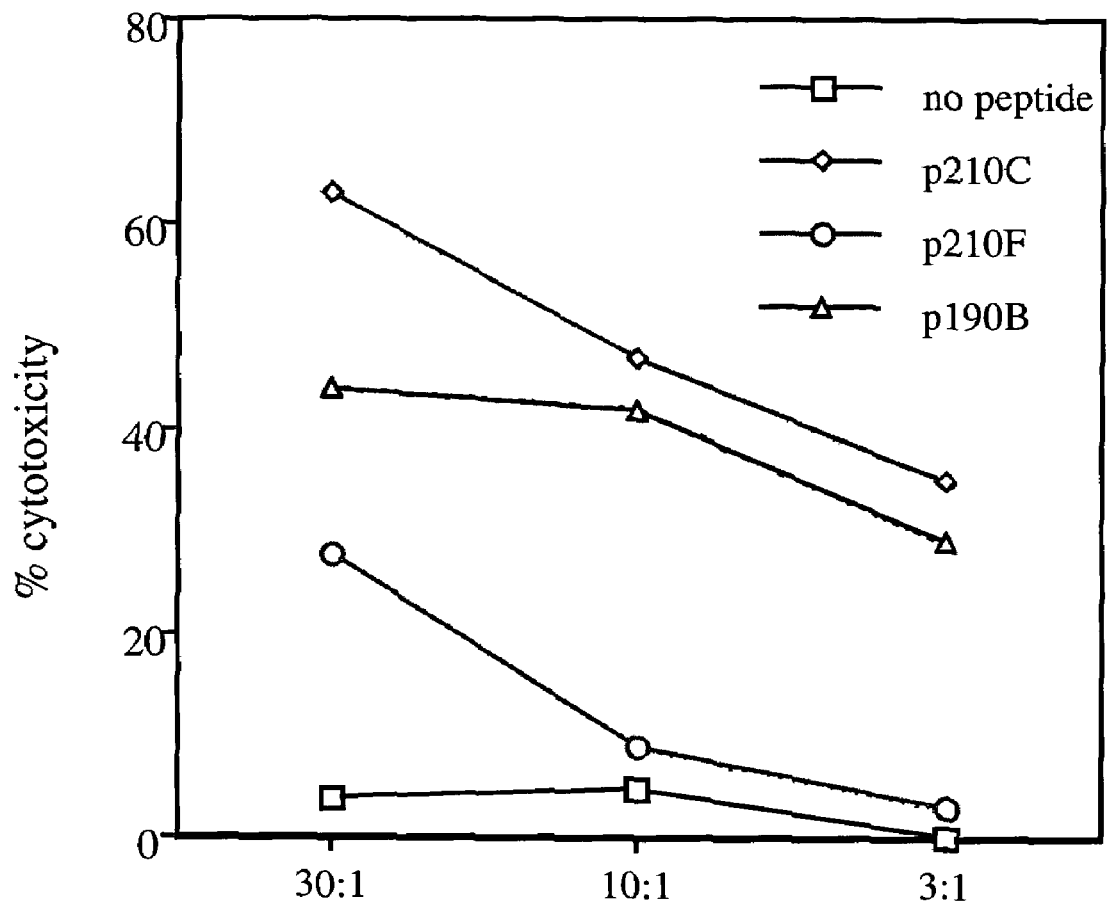

Gamma interferon ELISPOT is not always associated with functional killing. Therefore the T cell lines obtained after several stimulations with the analogue peptide were tested in a classic chromium-51 assay using peptide pulsed target cell lines. T cells generated in vitro in the presence of p210C (FIG. 4A) and b2a2 A3 (FIG. 4B) were able to kill T2 cell line pulsed with specific peptides but not without peptide or with control peptide. This experiment was also performed using HLA matched chronic myelogenous leukemia cell lines or CML blasts expressing the respective translocation b3a2 or b2a2. Significant cytotoxicity was generated raising the possibility that the native peptides were not naturally processed and/or sufficiently expressed in the surface of the leukemic cells.

EXAMPLE 12

Figure 5A:
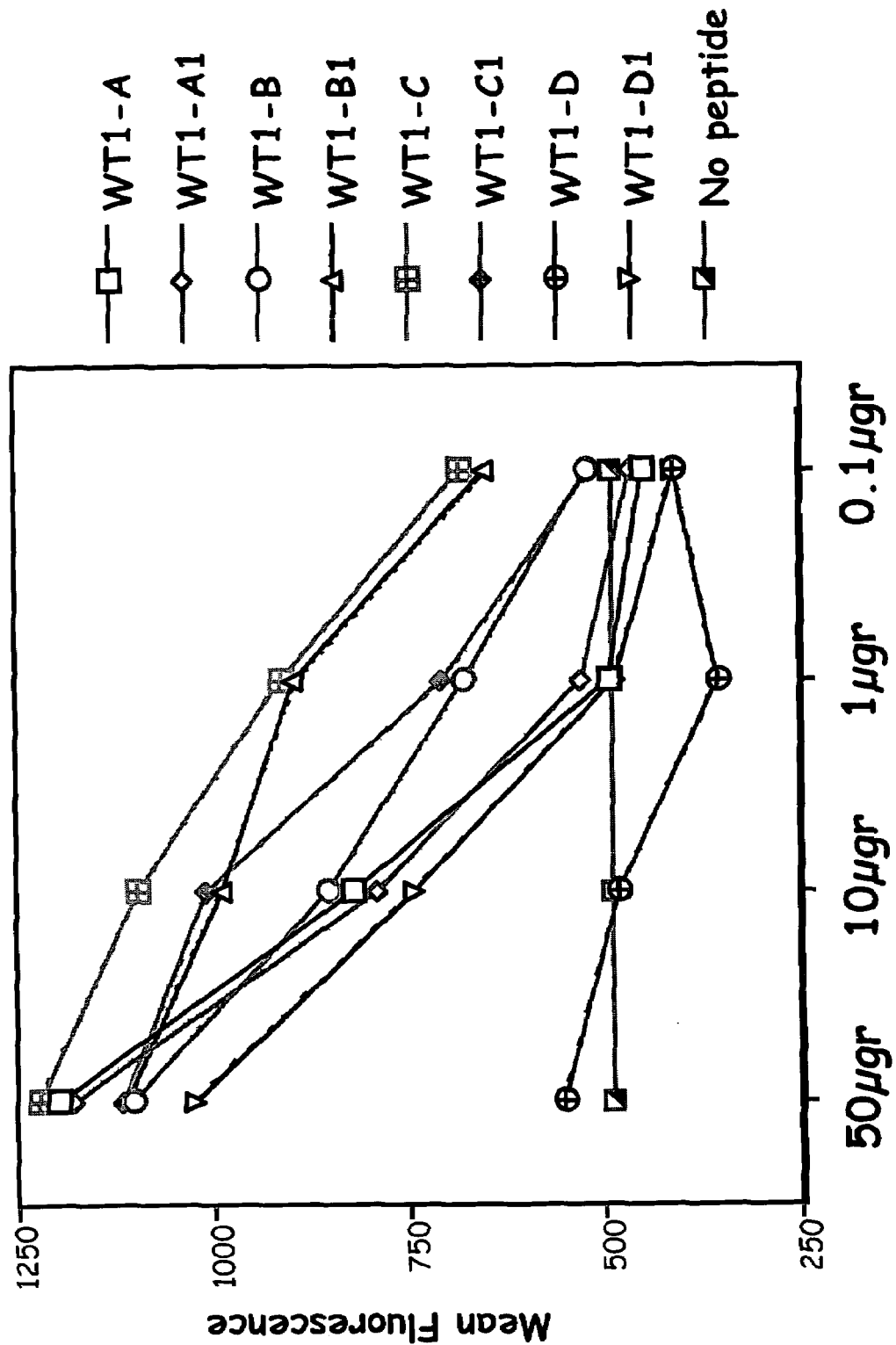
FIGS. 5A-5E show binding of native and synthetic WT-1 peptides to HLA A0201 cells (FIG. 5A) and to HLA A0301 cells (FIGS. 5B-5E).
Figure 5B:
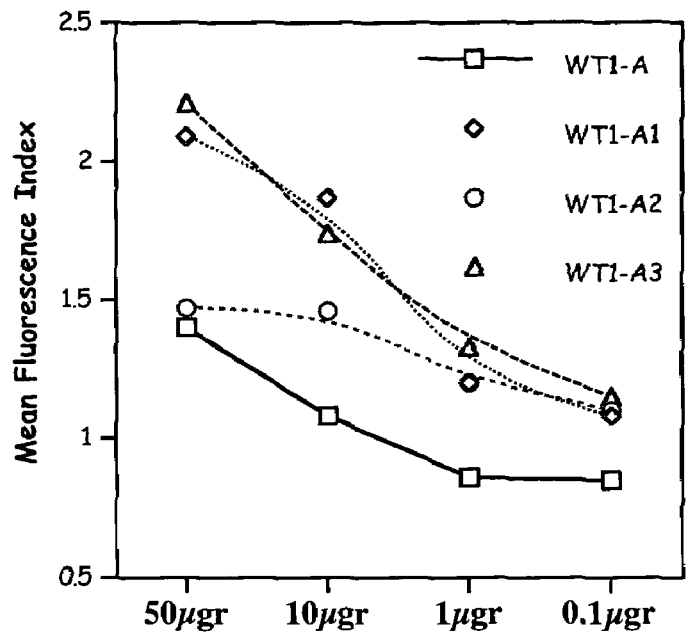
Figure 5C:
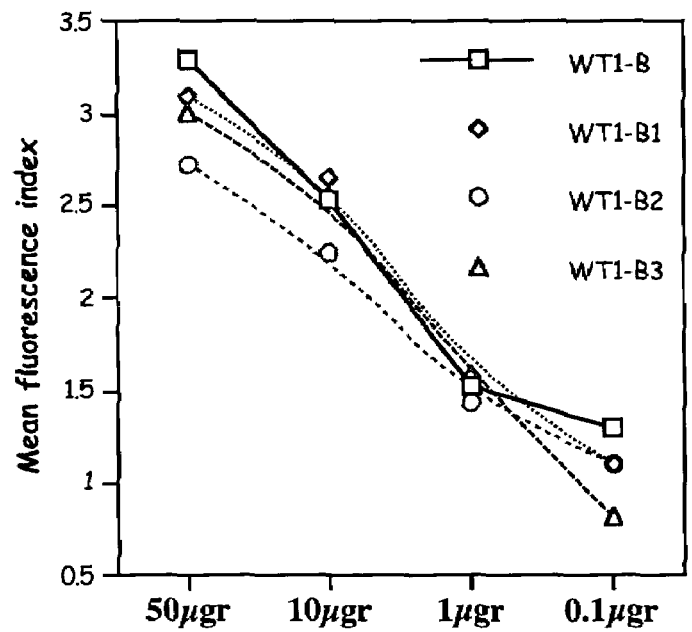
Figure 5D:
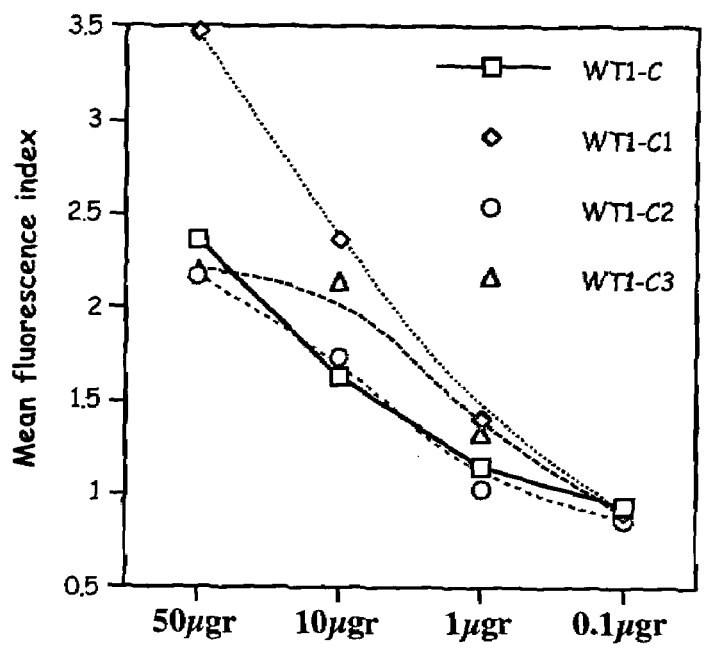
Figure 5E:
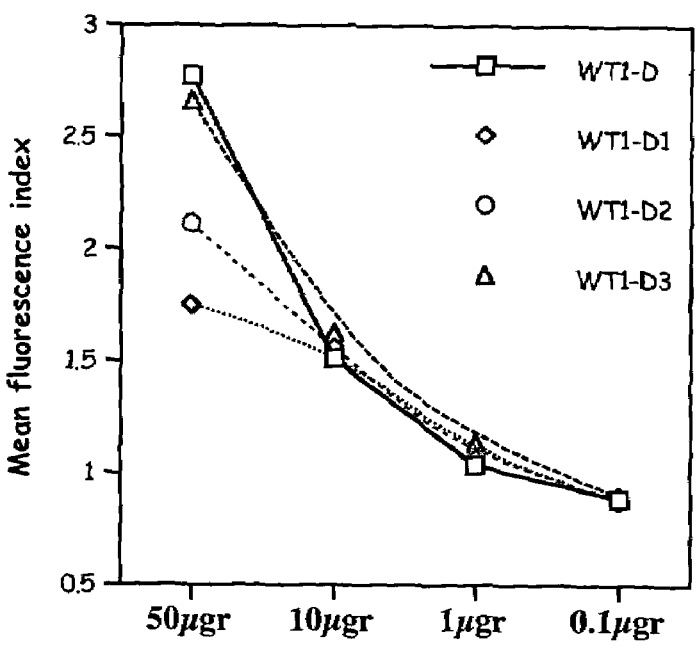

Binding of HLA-A0201 and -A0301 by Synthetic Peptide Analogues Derived from the WT1 Oncoprotein Thermostabilization assays using a TAP½ negative cell line (T2) and a modified protocol using Raji A0301 cells showed that several peptides that were predicted to be good binders to HLA A0201 or A0301 molecules, could stabilize MHC class I A0201 or A0301 molecules (Table 2). The synthetic analogues WT1-A1, -B1, C1, and -D1 all predicted to bind HLA A0201 better than the respective native WT-1 peptides demonstrated similar or increased binding compared to WT1-A, -B, C, and D (FIG. 5A). WT1-D1 demonstrated a significantly higher level of binding to HLA-A0201 over WT1-D which was similar to control. A comparison of HLA A0301 binding of A3WT 1-A, -B, -C, and -D with each of their respective three analogues demonstrated relatively similar binding (FIGS. 5B-5E).

EXAMPLE 13

Figure 6A:
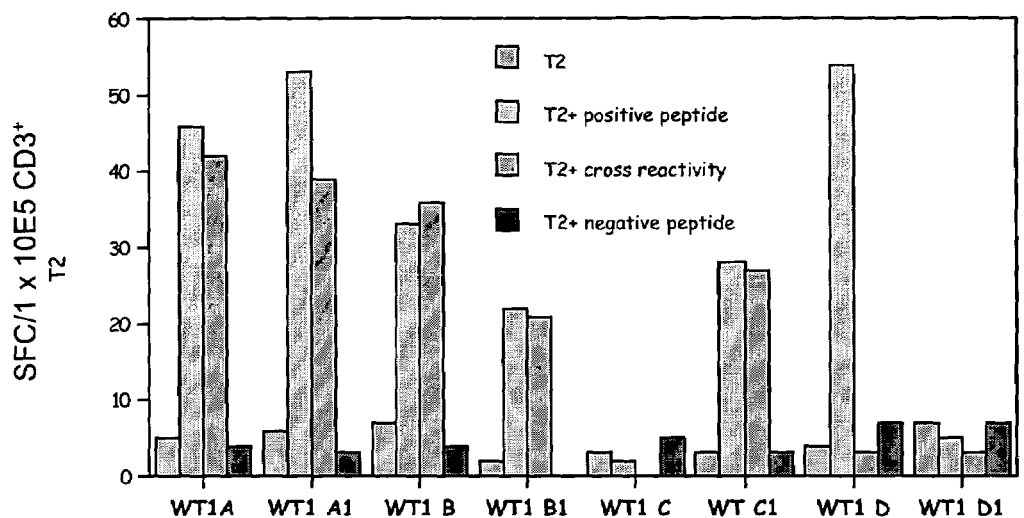
FIGS. 6A-6B show the results of a CD3+ gamma interferon ELISPOT (FIG. 6A) and cytotoxicity (FIG. 6B) from a healthy HLA A0201 donor against native and synthetic peptide pulsed T2 cells.
Figure 6B:
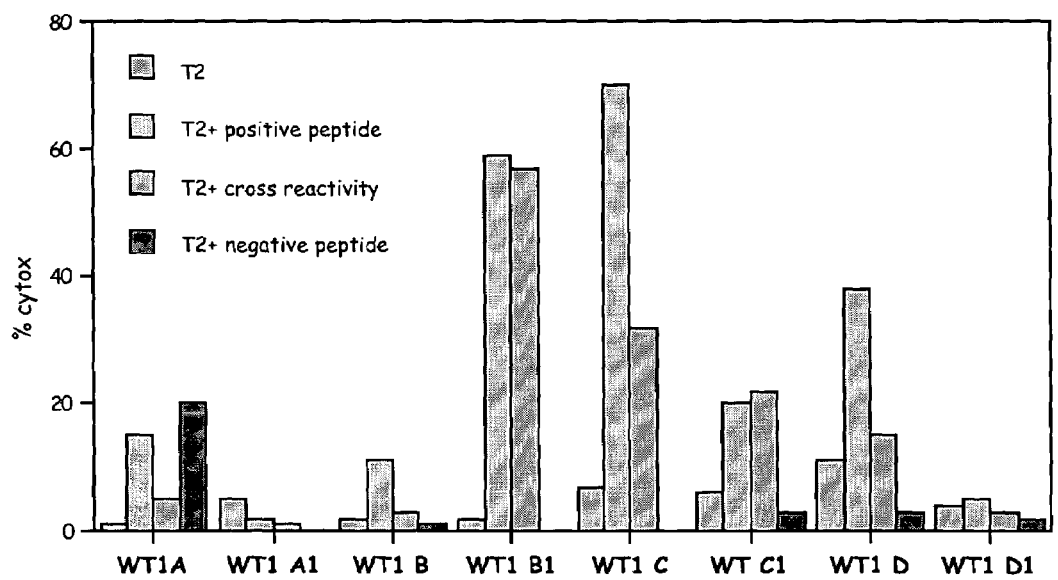
Figure 7A:
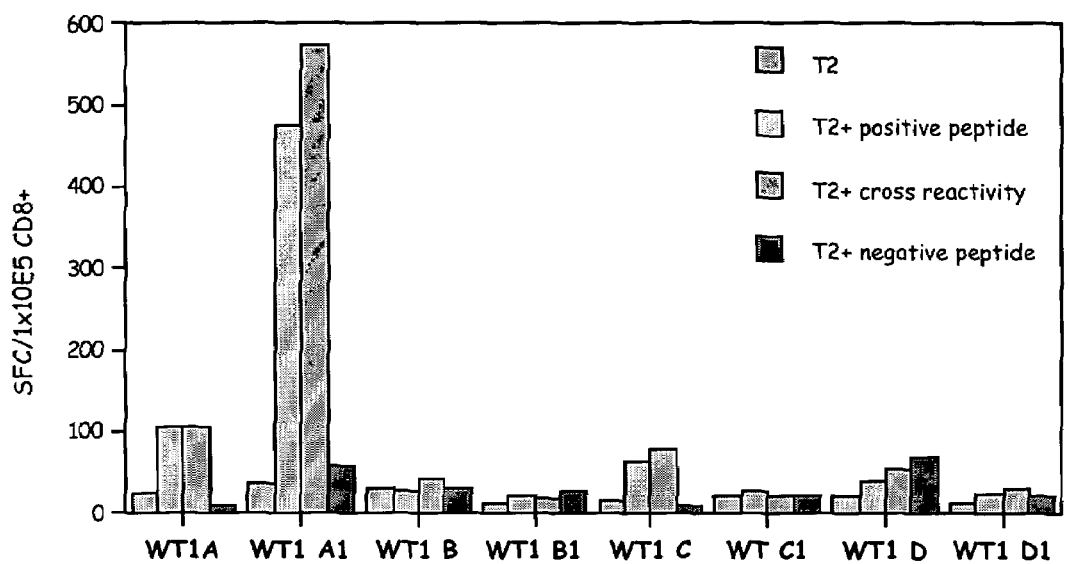
FIGS. 7A-7D show the results of a CD8+ (FIG. 7A) and CD3+ (FIGS. 7B-7D) gamma interferon ELISPOT from healthy HLA A0201 donors using native and synthetic WT-1 peptides.
Figure 7B:
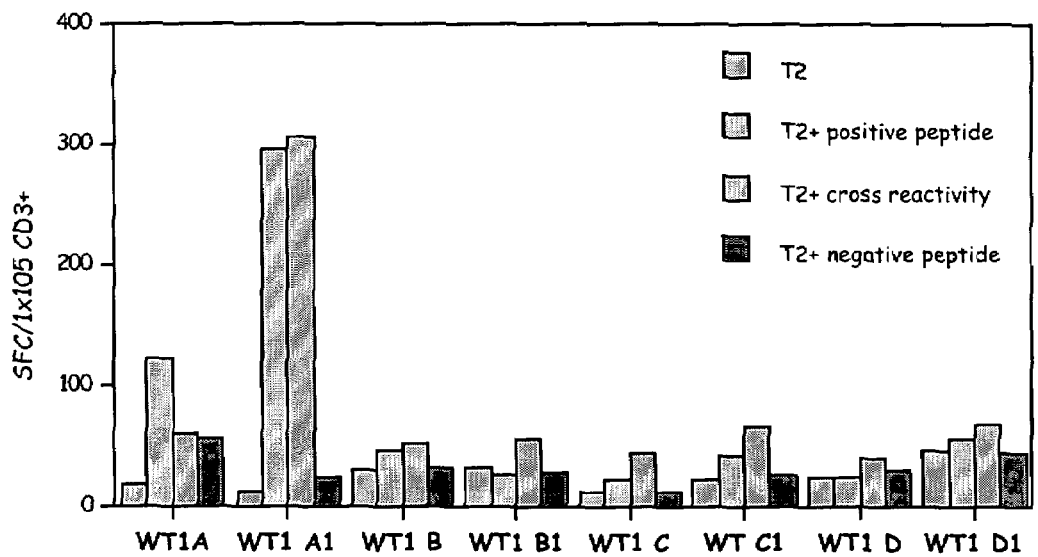
Figure 7C:
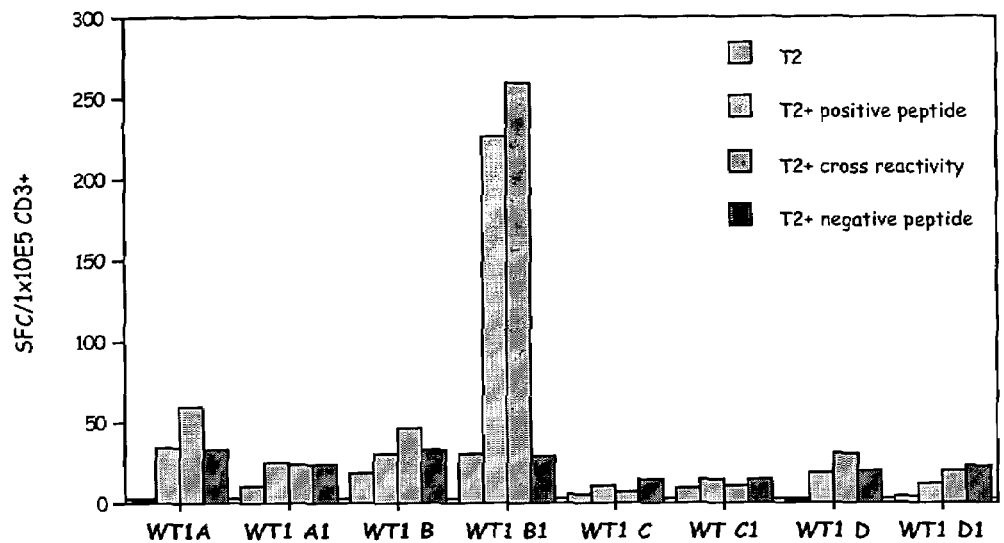
Figure 7D:
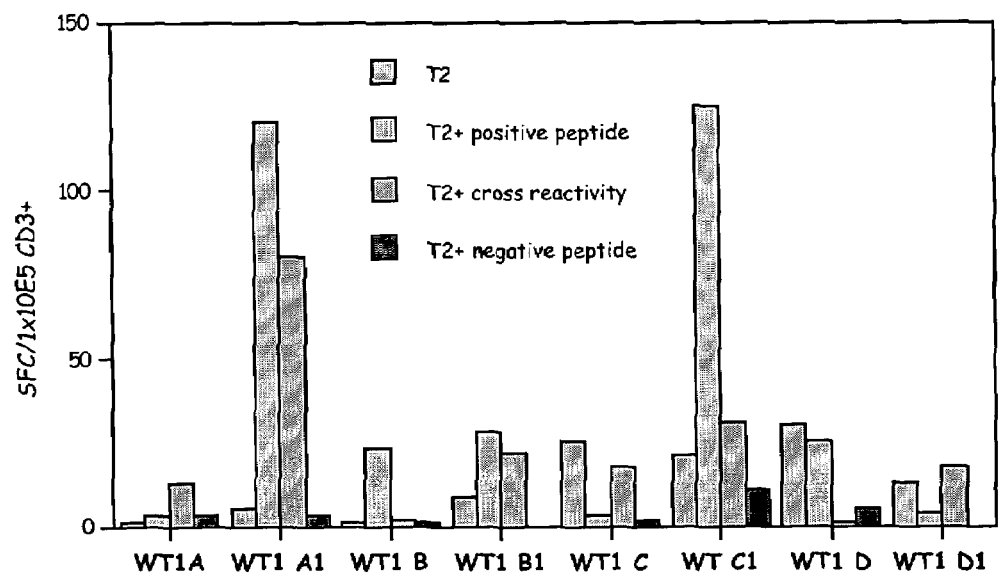
Figure 8A:
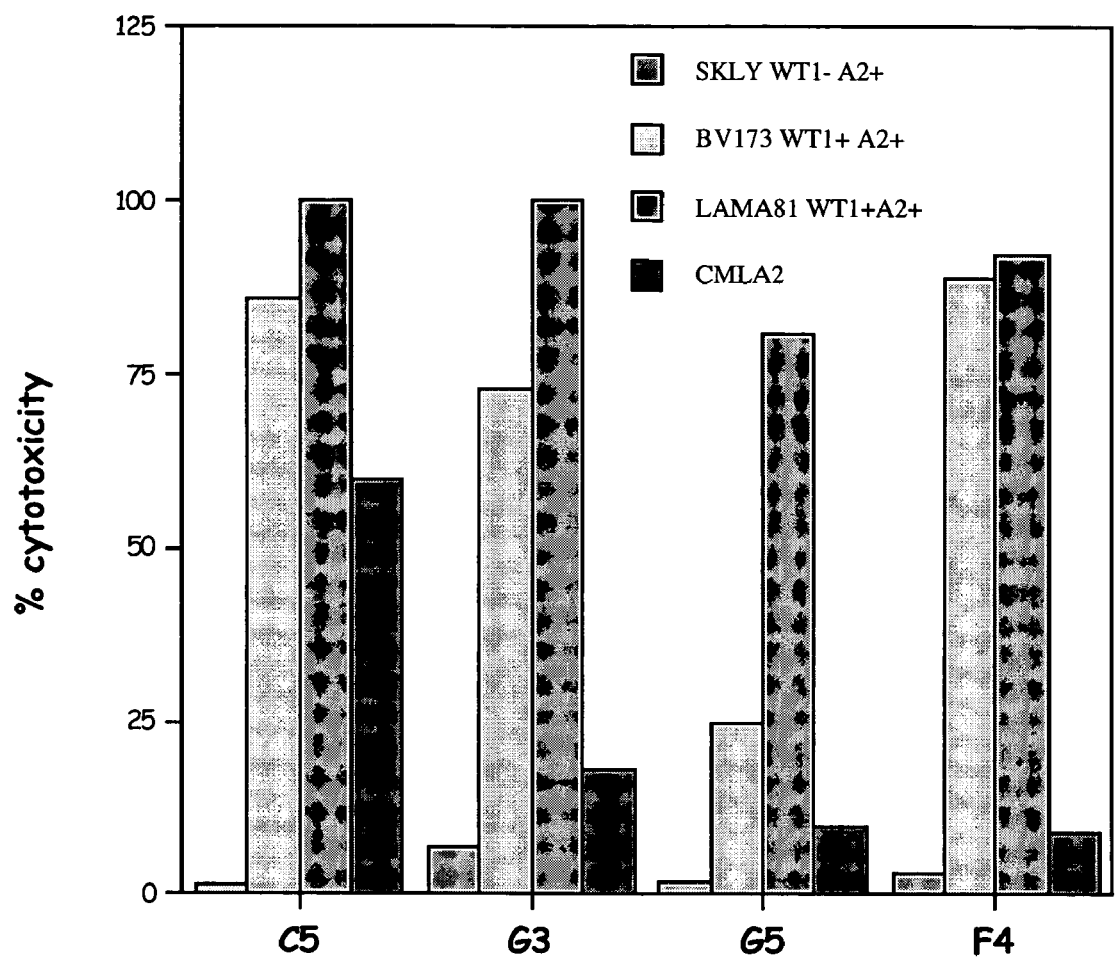

Induction of CD8 or CD3 Immune Response Against Synthetic Peptide Analogues Derived from the WT1 Oncoprotein Cells were primarily stimulated with autologous monocyte-derived, peptide-pulsed dendritic cells generated in the presence of GM-CSF, IL-4, TNF alpha, PGE2 and CD40L and re-stimulated with peptide-pulsed CD 14+ monocytes in the presence of IL-2 and IL-7. After two to four stimulations, the CD8+ CTL lines were assessed by either IFN alpha ELISPOT or a chromium release assay using pulsed, HLA-matched leukemic cell lines (FIGS. 6A-6B). Several analogue peptides generated greater immune responses, i.e., increased CD8 T cell precursor frequency, in comparison with the native peptides (FIGS. 7A-7D). CD8+ T cells stimulated with the new synthetic peptides cross-reacted with the native WT1 peptide sequence and are able to kill HLA matched chronic myelogenous leukemia blasts (FIGS. 8A-8B).

The following references are cited herein:
1. Kessler et al. J Exp Med, 185(4): p. 629-40 (1997).
2. Dyall et al. J Exp Med, 188(9): p. 1553-61 (1998).
3. Valmori et al. J Immunol, 165(1): p. 533-8 (2000).
4. Valmori et al. J Immunol, 164(2): p. 1125-31 (2000).

Any patents or publications mentioned in this specification are indicative of the levels of those skilled in the art to which the invention pertains. Further, these patents and publications are incorporated by reference herein to the same extent as if each individual publication was incorporated specifically and individually by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A synthetic peptide, comprising:
a sequence of amino acids containing at least a segment that is an analogue of a native peptide that specifically binds to HLA A0201 or HLA A0301 molecules on a cell characteristic of a pathophysiologic state in a mammal, wherein said segment comprises YMFPNAPYL (SEQ ID NO:18).

2. The synthetic peptide of claim 1, further comprising:
an immunogenic carrier linked thereto.

3. The synthetic peptide of claim 2, wherein said immunogenic carrier is a protein, a peptide or an antigen-presenting cell.

4. The synthetic peptide of claim 3, wherein said protein or peptide is keyhole limpet hemocyanin, an albumin or a polyamino acid.

5. The synthetic peptide of claim 3, wherein said antigen presenting cell is a dendritic cell.

6. A pharmaceutical composition, comprising:
a therapeutically effective amount of the synthetic peptide of claim 1; and
a pharmaceutically acceptable carrier.

7. An immunogenic composition comprising an immunogenically effective amount of the synthetic peptide of claim 1 and a pharmaceutically acceptable carrier, adjuvant or diluent or a combination thereof.

8. The immunogenic composition of claim 7, wherein said immunogenic carrier is a protein, a peptide or an antigen presenting cell linked to said synthetic peptide.

9. The immunogenic composition of claim 8, wherein said protein or peptide is keyhole limpet hemocyanin, an albumin or a polyamino acid.

10. The immunogenic composition of claim 8, wherein said antigen presenting cell is a dendritic cell.

* * * * *

SEQUENCE LISTING

```
<160> NUMBER OF SEQ ID NOS: 50

<210> SEQ ID NO 1
<211> LENGTH: 9
<212> TYPE: PRT
<213> ORGANISM: artificial sequence
<220> FEATURE:
<223> OTHER INFORMATION: native peptide CMLA2

<400> SEQUENCE: 1

Ser Ser Lys Ala Leu Gln Arg Pro Val
                5

<210> SEQ ID NO 2
<211> LENGTH: 9
<212> TYPE: PRT
<213> ORGANISM: artificial sequence
<220> FEATURE:
<223> OTHER INFORMATION: analogue peptide p210F

<400> SEQUENCE: 2

Tyr Leu Lys Ala Leu Gln Arg Pro Val
                5

<210> SEQ ID NO 3
<211> LENGTH: 9
<212> TYPE: PRT
<213> ORGANISM: artificial sequence
<220> FEATURE:
<223> OTHER INFORMATION: native peptide CMLA3

<400> SEQUENCE: 3

Lys Gln Ser Ser Lys Ala Leu Gln Arg
                5

<210> SEQ ID NO 4
<211> LENGTH: 9
<212> TYPE: PRT
```

```
<213> ORGANISM: artificial sequence
<220> FEATURE:
<223> OTHER INFORMATION: analogue peptide p210A

<400> SEQUENCE: 4

Lys Gln Ser Ser Lys Ala Leu Gln Val
                5

<210> SEQ ID NO 5
<211> LENGTH: 9
<212> TYPE: PRT
<213> ORGANISM: artificial sequence
<220> FEATURE:
<223> OTHER INFORMATION: analogue peptide p210B

<400> SEQUENCE: 5

Lys Leu Ser Ser Lys Ala Leu Gln Val
                5

<210> SEQ ID NO 6
<211> LENGTH: 9
<212> TYPE: PRT
<213> ORGANISM: artificial sequence
<220> FEATURE:
<223> OTHER INFORMATION: native peptide p219Cn

<400> SEQUENCE: 6

Lys Ala Leu Gln Arg Pro Val Ala Ser
                5

<210> SEQ ID NO 7
<211> LENGTH: 9
<212> TYPE: PRT
<213> ORGANISM: artificial sequence
<220> FEATURE:
<223> OTHER INFORMATION: analogue peptide p210C

<400> SEQUENCE: 7

Lys Leu Leu Gln Arg Pro Val Ala Val
                5

<210> SEQ ID NO 8
<211> LENGTH: 9
<212> TYPE: PRT
<213> ORGANISM: artificial sequence
<220> FEATURE:
<223> OTHER INFORMATION: native peptide p210Dn

<400> SEQUENCE: 8

Thr Gly Phe Lys Gln Ser Ser Lys Ala
                5

<210> SEQ ID NO 9
<211> LENGTH: 9
<212> TYPE: PRT
<213> ORGANISM: artificial sequence
<220> FEATURE:
<223> OTHER INFORMATION: analogue peptide p210D

<400> SEQUENCE: 9

Thr Leu Phe Lys Gln Ser Ser Lys Val
                5

<210> SEQ ID NO 10
<211> LENGTH: 9
<212> TYPE: PRT
<213> ORGANISM: artificial sequence
```

```
<220> FEATURE:
<223> OTHER INFORMATION: analogue peptide p210E

<400> SEQUENCE: 10

Tyr Leu Phe Lys Gln Ser Ser Lys Val
                5

<210> SEQ ID NO 11
<211> LENGTH: 9
<212> TYPE: PRT
<213> ORGANISM: artificial sequence
<220> FEATURE:
<223> OTHER INFORMATION: native peptide b3a2A

<400> SEQUENCE: 11

Leu Thr Ile Asn Lys Glu Glu Ala Leu
                5

<210> SEQ ID NO 12
<211> LENGTH: 9
<212> TYPE: PRT
<213> ORGANISM: artificial sequence
<220> FEATURE:
<223> OTHER INFORMATION: analogue peptide b3a2 A1

<400> SEQUENCE: 12

Leu Leu Ile Asn Lys Glu Glu Ala Leu
                5

<210> SEQ ID NO 13
<211> LENGTH: 9
<212> TYPE: PRT
<213> ORGANISM: artificial sequence
<220> FEATURE:
<223> OTHER INFORMATION: analogue peptide b3a2 A2

<400> SEQUENCE: 13

Leu Thr Ile Asn Lys Val Glu Ala Leu
                5

<210> SEQ ID NO 14
<211> LENGTH: 9
<212> TYPE: PRT
<213> ORGANISM: artificial sequence
<220> FEATURE:
<223> OTHER INFORMATION: analogue peptide b3a2 A3

<400> SEQUENCE: 14

Tyr Leu Ile Asn Lys Glu Glu Ala Leu
                5

<210> SEQ ID NO 15
<211> LENGTH: 9
<212> TYPE: PRT
<213> ORGANISM: artificial sequence
<220> FEATURE:
<223> OTHER INFORMATION: analogue peptide b3a2 A4

<400> SEQUENCE: 15

Tyr Leu Ile Asn Lys Glu Glu Ala Val
                5

<210> SEQ ID NO 16
<211> LENGTH: 9
<212> TYPE: PRT
<213> ORGANISM: artificial sequence
<220> FEATURE:
```

<223> OTHER INFORMATION: analogue peptide b3a2 A5

<400> SEQUENCE: 16

Tyr Leu Ile Asn Lys Val Glu Ala Leu
              5

<210> SEQ ID NO 17
<211> LENGTH: 9
<212> TYPE: PRT
<213> ORGANISM: artificial sequence
<220> FEATURE:
<223> OTHER INFORMATION: native peptide WT-1A

<400> SEQUENCE: 17

Arg Met Phe Pro Asn Ala Pro Tyr Leu
              5

<210> SEQ ID NO 18
<211> LENGTH: 9
<212> TYPE: PRT
<213> ORGANISM: artificial sequence
<220> FEATURE:
<223> OTHER INFORMATION: analogue peptide WT-1 A1

<400> SEQUENCE: 18

Tyr Met Phe Pro Asn Ala Pro Tyr Leu
              5

<210> SEQ ID NO 19
<211> LENGTH: 9
<212> TYPE: PRT
<213> ORGANISM: artificial sequence
<220> FEATURE:
<223> OTHER INFORMATION: native peptide WT-1 B1

<400> SEQUENCE: 19

Ser Leu Gly Glu Gln Gln Tyr Ser Val
              5

<210> SEQ ID NO 20
<211> LENGTH: 9
<212> TYPE: PRT
<213> ORGANISM: artificial sequence
<220> FEATURE:
<223> OTHER INFORMATION: analogue peptide WT-1 B1

<400> SEQUENCE: 20

Tyr Leu Gly Glu Gln Gln Tyr Ser Val
              5

<210> SEQ ID NO 21
<211> LENGTH: 9
<212> TYPE: PRT
<213> ORGANISM: artificial sequence
<220> FEATURE:
<223> OTHER INFORMATION: native peptide WT-1 C

<400> SEQUENCE: 21

Ala Leu Leu Pro Ala Val Pro Ser Leu
              5

<210> SEQ ID NO 22
<211> LENGTH: 9
<212> TYPE: PRT
<213> ORGANISM: artificial sequence
<220> FEATURE:
<223> OTHER INFORMATION: analogue peptide WT-1 C1

```
<400> SEQUENCE: 22

Tyr Leu Leu Pro Ala Val Pro Ser Leu
                5

<210> SEQ ID NO 23
<211> LENGTH: 9
<212> TYPE: PRT
<213> ORGANISM: artificial sequence
<220> FEATURE:
<223> OTHER INFORMATION: native peptide WT-1 D

<400> SEQUENCE: 23

Asn Leu Gly Ala Thr Leu Lys Gly Val
                5

<210> SEQ ID NO 24
<211> LENGTH: 9
<212> TYPE: PRT
<213> ORGANISM: artificial sequence
<220> FEATURE:
<223> OTHER INFORMATION: analogue peptide WT-1 D1

<400> SEQUENCE: 24

Tyr Leu Gly Ala Thr Leu Lys Gly Val
                5

<210> SEQ ID NO 25
<211> LENGTH: 9
<212> TYPE: PRT
<213> ORGANISM: artificial sequence
<220> FEATURE:
<223> OTHER INFORMATION: native peptide WT-1 E

<400> SEQUENCE: 25

Asp Leu Asn Ala Leu Leu Pro Ala Val
                5

<210> SEQ ID NO 26
<211> LENGTH: 9
<212> TYPE: PRT
<213> ORGANISM: artificial sequence
<220> FEATURE:
<223> OTHER INFORMATION: analogue peptide WT-1 E1

<400> SEQUENCE: 26

Tyr Leu Asn Ala Leu Leu Pro Ala Val
                5

<210> SEQ ID NO 27
<211> LENGTH: 9
<212> TYPE: PRT
<213> ORGANISM: artificial sequence
<220> FEATURE:
<223> OTHER INFORMATION: native peptide WT-1 F

<400> SEQUENCE: 27

Gly Val Phe Arg Gly Ile Gln Asp Val
                5

<210> SEQ ID NO 28
<211> LENGTH: 9
<212> TYPE: PRT
<213> ORGANISM: artificial sequence
<220> FEATURE:
<223> OTHER INFORMATION: analogue peptide WT-1 F1
```

```
<400> SEQUENCE: 28

Gly Leu Arg Arg Gly Ile Gln Asp Val
              5

<210> SEQ ID NO 29
<211> LENGTH: 9
<212> TYPE: PRT
<213> ORGANISM: artificial sequence
<220> FEATURE:
<223> OTHER INFORMATION: native peptide WT-1 G

<400> SEQUENCE: 29

Lys Arg Tyr Phe Lys Leu Ser His Leu
              5

<210> SEQ ID NO 30
<211> LENGTH: 9
<212> TYPE: PRT
<213> ORGANISM: artificial sequence
<220> FEATURE:
<223> OTHER INFORMATION: analogue peptide WT-1 G1

<400> SEQUENCE: 30

Lys Leu Tyr Phe Lys Leu Ser His Leu
              5

<210> SEQ ID NO 31
<211> LENGTH: 9
<212> TYPE: PRT
<213> ORGANISM: artificial sequence
<220> FEATURE:
<223> OTHER INFORMATION: native peptide WT-1 H

<400> SEQUENCE: 31

Ala Leu Leu Leu Arg Thr  Pro Tyr Ser
              5

<210> SEQ ID NO 32
<211> LENGTH: 9
<212> TYPE: PRT
<213> ORGANISM: artificial sequence
<220> FEATURE:
<223> OTHER INFORMATION: analogue peptide WT-1 H1

<400> SEQUENCE: 32

Ala Leu Leu Leu Arg Thr Pro Tyr Val
              5

<210> SEQ ID NO 33
<211> LENGTH: 9
<212> TYPE: PRT
<213> ORGANISM: artificial sequence
<220> FEATURE:
<223> OTHER INFORMATION: native peptide WT-1 J

<400> SEQUENCE: 33

Cys Met Thr Trp Asn Gln Met Asn Leu
              5

<210> SEQ ID NO 34
<211> LENGTH: 9
<212> TYPE: PRT
<213> ORGANISM: artificial sequence
<220> FEATURE:
<223> OTHER INFORMATION: analogue peptide WT-1 J1

<400> SEQUENCE: 34
```

Tyr Met Thr Trp Asn Gln Met Asn Leu
            5

<210> SEQ ID NO 35
<211> LENGTH: 9
<212> TYPE: PRT
<213> ORGANISM: artificial sequence
<220> FEATURE:
<223> OTHER INFORMATION: native peptide A3WT-1 A

<400> SEQUENCE: 35

Asn Met His Gln Arg Asn Met Thr Lys
            5

<210> SEQ ID NO 36
<211> LENGTH: 9
<212> TYPE: PRT
<213> ORGANISM: artificial sequence
<220> FEATURE:
<223> OTHER INFORMATION: analogue peptide A3WT-1 A1

<400> SEQUENCE: 36

Asn Met Tyr Gln Arg Asn Met Thr Lys
            5

<210> SEQ ID NO 37
<211> LENGTH: 9
<212> TYPE: PRT
<213> ORGANISM: artificial sequence
<220> FEATURE:
<223> OTHER INFORMATION: analogue peptide A3WT-1 A2

<400> SEQUENCE: 37

Asn Met His Gln Arg Val Met Thr Lys
            5

<210> SEQ ID NO 38
<211> LENGTH: 9
<212> TYPE: PRT
<213> ORGANISM: artificial sequence
<220> FEATURE:
<223> OTHER INFORMATION: analogue peptide A3WT-1 A3

<400> SEQUENCE: 38

Asn Met Tyr Gln Arg Val Met Thr Lys
            5

<210> SEQ ID NO 39
<211> LENGTH: 9
<212> TYPE: PRT
<213> ORGANISM: artificial sequence
<220> FEATURE:
<223> OTHER INFORMATION: native peptide A3WT-1 B

<400> SEQUENCE: 39

Gln Met Asn Leu Gly Ala Thr Leu Lys
            5

<210> SEQ ID NO 40
<211> LENGTH: 9
<212> TYPE: PRT
<213> ORGANISM: artificial sequence
<220> FEATURE:
<223> OTHER INFORMATION: analogue peptide of A3WT-1 B1

<400> SEQUENCE: 40

Gln Met Tyr Leu Gly Ala Thr Leu Lys
                5

<210> SEQ ID NO 41
<211> LENGTH: 9
<212> TYPE: PRT
<213> ORGANISM: artificial sequence
<220> FEATURE:
<223> OTHER INFORMATION: analogue peptide A3WT-1 B2

<400> SEQUENCE: 41

Gln Met Asn Leu Gly Val Thr Leu Lys
                5

<210> SEQ ID NO 42
<211> LENGTH: 9
<212> TYPE: PRT
<213> ORGANISM: artificial sequence
<220> FEATURE:
<223> OTHER INFORMATION: analogue peptide A3WT-1 B3

<400> SEQUENCE: 42

Gln Met Tyr Leu Gly Val Thr Leu Lys
                5

<210> SEQ ID NO 43
<211> LENGTH: 10
<212> TYPE: PRT
<213> ORGANISM: artificial sequence
<220> FEATURE:
<223> OTHER INFORMATION: native peptide A3WT-1 C

<400> SEQUENCE: 43

Phe Met Cys Ala Tyr Pro Gly Cys Asn Lys
                5                   10

<210> SEQ ID NO 44
<211> LENGTH: 10
<212> TYPE: PRT
<213> ORGANISM: artificial sequence
<220> FEATURE:
<223> OTHER INFORMATION: analogue peptide A3WT-1 C1

<400> SEQUENCE: 44

Phe Met Tyr Ala Tyr Pro Gly Cys Asn Lys
                5                   10

<210> SEQ ID NO 45
<211> LENGTH: 10
<212> TYPE: PRT
<213> ORGANISM: artificial sequence
<220> FEATURE:
<223> OTHER INFORMATION: analogue peptide A3WT-1 C2

<400> SEQUENCE: 45

Phe Met Cys Ala Tyr Pro Phe Cys Asn Lys
                5                   10

<210> SEQ ID NO 46
<211> LENGTH: 10
<212> TYPE: PRT
<213> ORGANISM: artificial sequence
<220> FEATURE:
<223> OTHER INFORMATION: analogue peptide A3WT-1 C3

<400> SEQUENCE: 46

Phe Met Tyr Ala Tyr Pro Phe Cys Asn Lys

-continued

<210> SEQ ID NO 47
<211> LENGTH: 10
<212> TYPE: PRT
<213> ORGANISM: artificial sequence
<220> FEATURE:
<223> OTHER INFORMATION: native peptide A3WT-1 D

<400> SEQUENCE: 47

Lys Leu Ser His Leu Gln Met His Ser Arg
                5                   10

<210> SEQ ID NO 48
<211> LENGTH: 10
<212> TYPE: PRT
<213> ORGANISM: artificial sequence
<220> FEATURE:
<223> OTHER INFORMATION: analogue peptide A3WT-1 D1

<400> SEQUENCE: 48

Lys Leu Tyr His Leu Gln Met His Ser Arg
                5                   10

<210> SEQ ID NO 49
<211> LENGTH: 10
<212> TYPE: PRT
<213> ORGANISM: artificial sequence
<220> FEATURE:
<223> OTHER INFORMATION: analogue peptide A3WT-1 D2

<400> SEQUENCE: 49

Lys Leu Ser His Leu Gln Met His Ser Lys
                5                   10

<210> SEQ ID NO 50
<211> LENGTH: 10
<212> TYPE: PRT
<213> ORGANISM: artificial sequence
<220> FEATURE:
<223> OTHER INFORMATION: analogue peptide A3WT-1 D3

<400> SEQUENCE: 50

Lys Leu Tyr His Leu Gln Met His Ser Lys
                5                   10